(12) United States Patent
Zhang et al.

(10) Patent No.: US 9,276,063 B2
(45) Date of Patent: Mar. 1, 2016

(54) GOLD NANOSTRUCTURES AND METHODS OF USE

(75) Inventors: Jin Z. Zhang, Santa Cruz, CA (US); Adam Schwartzberg, Santa Cruz, CA (US); Tammy Y. Olson, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 936 days.

(21) Appl. No.: 13/284,880

(22) Filed: Oct. 29, 2011

(65) Prior Publication Data

US 2012/0045754 A1 Feb. 23, 2012

Related U.S. Application Data

(62) Division of application No. 11/784,297, filed on Apr. 5, 2007, now Pat. No. 8,137,759.

(60) Provisional application No. 60/790,317, filed on Apr. 7, 2006.

(51) Int. Cl.
*H01L 29/06* (2006.01)
*B82Y 10/00* (2011.01)
*B82Y 25/00* (2011.01)
*B82Y 30/00* (2011.01)
*G01N 21/552* (2014.01)
*G01N 21/65* (2006.01)
*G01N 33/543* (2006.01)
*H01L 29/12* (2006.01)
*H01F 1/00* (2006.01)
*B22F 1/00* (2006.01)

(52) U.S. Cl.
CPC .......... *H01L 29/0665* (2013.01); *B22F 1/0025* (2013.01); *B82Y 10/00* (2013.01); *B82Y 25/00* (2013.01); *B82Y 30/00* (2013.01); *G01N 21/554* (2013.01); *G01N 21/658* (2013.01); *G01N 33/5432* (2013.01); *G01N 33/54346* (2013.01); *H01F 1/0054* (2013.01); *H01L 29/0673* (2013.01); *H01L 29/127* (2013.01); *B22F 2001/0029* (2013.01); *B22F 2998/00* (2013.01); *Y10T 428/12431* (2015.01); *Y10T 428/2975* (2015.01); *Y10T 428/2982* (2015.01)

(58) Field of Classification Search
CPC .... H01L 29/0665; B82Y 10/00; B82Y 25/00; B82Y 30/00; G01N 21/554; G01N 21/658; G01N 33/5432; G01N 33/54346
See application file for complete search history.

(56) References Cited

U.S. PATENT DOCUMENTS

| | | | | |
|---|---|---|---|---|
| 7,098,144 | B2 * | 8/2006 | Zhang et al. | 438/734 |
| 2002/0070426 | A1 * | 6/2002 | Cumings et al. | 257/613 |
| 2003/0089899 | A1 * | 5/2003 | Lieber et al. | 257/9 |
| 2004/0043527 | A1 * | 3/2004 | Bradley | B82Y 15/00 438/48 |
| 2006/0273328 | A1 * | 12/2006 | Niu | H01L 33/20 257/79 |
| 2007/0089564 | A1 * | 4/2007 | Tung | 75/370 |

OTHER PUBLICATIONS

Murphy et al., Anisotropic Metal Nanoparticles: Synthesis, Assembly and Optical Applications, 2005, J. Phys. Chem., vol. 109, pp. 13857-13870.*

Kijima et al., Noble Metal nanotubes (Pt, Pd, Ag) from Lyotropic Mixed-Surfactant Liquid-Crystal Templates, Angew. Chem. 2004, vol. 116, pp. 230-234.*

Norman, T., Grant, C., Magana, D., Anderson, Zhang, J., Cao, D., Bridges, F., Liu, J., and van Buuren, T., *Longitudinal Plasma Resonance Shifts in Gold Nanoparticle Aggregates.* 2002 Proc. of SPIE, 4807: 51-58.

Hao, E., Li, S., Bailey, R.C., Zou, S., Schatz, G.C., and Hupp, J.T., *Optical Properties of Metal Nanoshells.* 2004 J. Phys. Chem. B. 108: 1224-1229.

Chen, J., Saeki, F., Wiley, B.J., Cang, H., Cobb, M.J., Li, Z.-Y., Au, L., Zhang, H., Kimmey, M.B., Li, Z., and Xia, Y. *Gold Nanocages: Bioconjugation and their Potential use as Optical Imaging Contrast Agents,* 2005 Nano Lett., 5(3): 473-477.

Liang, H.-P., Zhang, H.-M., Hu, J.-S., Guo, Y.-G., Wan, L.-J., and Bai, C.-L., *Pt Hollow Nanospheres: Facile Synthesis and Enhanced Electrocatalysts.* 2004 Angew. Chem. Int. Ed. 43: 1540-1543.

Liang, H.P., Wan, L.-J., Bai, C.-L., and Jiang, L. *Gold Hollow Nanospheres: Tunable Surface Plasmon Resonance Controlled by Interior-Cavity Sizes* 2005 J. Phys. Chem. B 109: 7795-7800.

Wu, C., Liang, X., and Jiang, H. *Metal Nanoshells as a Contrast Agent in Near-Infrared diffuse Optical Tomography.* 2005 Optics Communications 253: 214-221.

Schwartzberg, A.M., Olson, T.Y., Talley, C.E., and Zhang, J.Z. *Synthesis, Characterization, and Tunable Optical Properties of Hollow Gold Nanospheres* 2006 J. Phys. Chem. B 110:19935-19944.

Zhang, J.Z., *Biomedical Applications of Shape-Controlled Plasmonic Nanostructures: A Case Study of Hollow Gold Nanospheres for Photothermal Abalation Therapy of Cancer.* 2010 J. Phys. Chem. Lett. 1: 686-695.

* cited by examiner

*Primary Examiner* — Melanie Y Brown

(74) *Attorney, Agent, or Firm* — Matthew Kaser; Adam Bell

(57) ABSTRACT

The invention is drawn to novel nanostructures comprising hollow nanospheres and nanotubes for use as chemical sensors, conduits for fluids, and electronic conductors. The nanostructures can be used in microfluidic devices, for transporting fluids between devices and structures in analytical devices, for conducting electrical currents between devices and structure in analytical devices, and for conducting electrical currents between biological molecules and electronic devices, such as bio-microchips.

8 Claims, 13 Drawing Sheets

GOLD NANOSTRUCTURES AND METHODS OF USE

This application is a divisional of U.S. application Ser. No. 11/784,297 filed 5 Apr., 2007 now U.S. Pat. No. 8,137,759 titled "Novel Gold Nanostructures And Methods Of Use", which itself present application claims priority to U.S. Provisional Patent Application Ser. No. 60/790,317 entitled "Synthesis Of Hollow Gold Nanoshells And Methods Of Use" filed Apr. 7, 2006, which is herein incorporated by reference in its entirety for all purposes. The present application claims priority to and the benefit of the above application Ser. No. 11/784,297 and 60/790,317.

This invention was made partly using funds from the National Science Foundation, the Petroleum Research Fund/American Chemical Society, the University of California at Santa Cruz, the student employee graduate research fellowship at Lawrence Livermore National Laboratory. This work was performed under the auspices of the U.S. Department of Energy by University of California Lawrence Livermore National Laboratory under contract No. W-7405-Eng-48. The US Federal Government may have certain rights to this invention.

FIELD OF THE INVENTION

The present invention relates to structures comprising a metal with useful properties. The structures are hollow spheres and tubes. The invention further relates to methods of using the structures for detecting chemical and biological analytes and use in electronics and in microfluidics.

BACKGROUND

During the 1980s Raman Scattering in fibers was demonstrated by Lin, Stolen, and other co-workers of AT&T Bell Laboratories in Holmdel, N.J., using lasers operating between 0.3 µm to 2.0 µm. In the early years of the Raman fiber before extensive work had begun, no one perceived that a Raman fiber could be pumped by a practical semiconductor laser-based source or that an efficient CW-pumped Raman Fiber Laser was possible. However, with the development of Cladding-pumped Fiber Lasers and Fiber Bragg Gratings, diode-laser-based CW Raman Fiber Lasers have been made efficient, emitting at various wavelengths throughout the infrared spectrum a reality. (See van Gisbergen et al., (1996) Chem. Phys. Lett. 259: 599-604.)

Raman spectroscopy is a powerful optical technique for detecting and analyzing molecules. Its principle is based on detecting light scattered off a molecule that is shifted in energy with respect to the incident light. The shift, called Raman shift, is characteristic of individual molecules, reflecting their vibrational frequencies like molecular fingerprints. As a result, the key advantage of Raman spectroscopy is its molecular specificity while its main limitation is the small signal due to low quantum yield of Raman scattering. One way to enhance the Raman signal is to tune the excitation wavelength to be on resonance with an electronic transition, so called resonance Raman scattering. This can usually produce an enhancement on the order of $10^2$-$10^3$.

Another technique to enhance Raman scattering is surface enhancement by roughened metal surfaces, notably silver and gold, that provides an enhancement factor on the order of $10^6$-$10^8$. This is termed surface enhanced Raman spectroscopy (SERS). Similar or somewhat larger enhancement factors (~$10^8$-$10^{10}$) have been observed for metal, mostly silver or gold, nanoparticles.

In the last few years, it has been shown that an even larger enhancement (~$10^{10}$-$10^{15}$) is possible for aggregates of metal nanoparticles (MNPs), silver and gold. The largest enhancement factor of $10^{14}$-$10^{15}$ has been reported for rhodamine 6G (R6G) on single silver nanoparticle aggregates. This huge enhancement is thought to be mainly due to significant enhancement of the local electromagnetic field of the nanoparticle aggregate that strongly absorbs the incident excitation light for the Raman scattering process. With such large enhancement, many important molecules that are difficult to detect with Raman normally can now be easily detected. This opens many interesting and new opportunities for detecting and analyzing molecules using SERS with extremely high sensitivity and molecular specificity.

SERS can also be developed into a molecular imaging technique for biomedical and other applications. Existing Raman imaging equipment should be usable for SERS imaging. SERS will provide a much-enhanced signal and thereby significantly shortened data acquisition time, making the technique practically useful for medical or other commercial and industrial applications including chip inspection or chemical monitoring. SERS is also useful for detecting other cancer biomarkers that can interact or bind to the MNP surface. For example, Sutphen et al. have recently shown that lysophospholipids (LPL) are potential biomarkers of ovarian cancer (Sutphen et al., (2004) Cancer Epidemiol. Biomarker Prev. 13: 1185-1191).

For many practical applications, for example SERS and optical filters, it is highly desirable to narrow the distribution of size/shape of nanoparticle aggregates. For SERS in particular, the incident light has to be on resonance with the substrate absorption. Only those nanoparticle aggregates that have resonance absorption of the incident light are expected to be SERS active. It is thus extremely beneficial to have a narrow size/shape distribution and thereby narrow optical absorption.

Fluorescent nanoparticles (quantum dots (QDs) such as semiconductor quantum dots, SQDs) have been used recently as fluorescent biological markers and have been found to be extremely effective. They offer advantages including higher stability, stronger fluorescence, tunability of color, and possibility of optical encoding based on different sized or colored SQDs.

Metal nanoparticles have been recognized for their unique optical properties that could be exploited in optoelectronic devices. Nanoparticle systems composed of gold, for example, have distinct optical properties that make them amenable to study by Raman scattering. The Raman spectrum of the adsorbed species is significantly enhanced by 10 to 15 orders of magnitude when the metal nanoparticles have aggregated, leading to enhanced electromagnetic field effects near the surface that increases the Raman scattering intensity. The greater sensitivity found in the SERS of metal nanoparticle aggregates facilitates the detection and analysis of a whole host of molecules that were previously difficult to study.

Wang et al. disclose a method of using SQDs (dye-conjugated CdTe nanoparticles, CT-NPs) to detect interactive binding between Ag-CT-NPs and Ab-CT-NPs (Wang et al., (2002) NanoLett. 2: 817-822). The interactions were determined by differential quenching or enhancement fluorescence activity of two different sized SQDs (red or green) measured during the analysis.

The use of SERS for analyte detection of biomolecules has been previously studied. U.S. Pat. No. 6,699,724 to West et al. describes a chemical sensing device and method (nanoshell-modified ELISA technique) based on the enzyme-linked immunoadsorbant assay (ELISA). The chemical sensing device can comprise a core comprising gold sulfide and a surface capable of inducing surface enhanced Raman scattering (SERS). In much of the patent disclosure, the nanoparticle is disclosed as having a silica core and a gold shell. The patent discloses that an enhancement of 600,000-fold ($6\times10^5$) in the Raman signal using conjugated mercaptoaniline was observed.

In the nanoshell-modified ELISA technique, antibodies are directly bound to the metal nanoshells. Raman spectra are taken of the antibody-nanoshell conjugates before and after the addition of a sample containing a possible antigen, and binding of antigen to antibody is expected to cause a detectable shift in the spectra.

The conjugation of quantum dots to antibodies used for ultrasensitive nonisotopic detection for use in biological assays has also been studied. U.S. Pat. No. 6,468,808 B1 to Nie et al. disclosed an antibody is conjugated to a water-soluble quantum dot. The binding of the quantum dot-antibody conjugate to a targeted protein will result in agglutination, which can be detected using an epi-fluorescence microscope. In addition, Nie et al. described a system in which a quantum dot is attached to one end of an oligonucleotide and a quenching moiety is attached to the other. The preferred quenching moiety in the Nie patent is a nonfluorescent organic chromophore such as 4-[4'-dimethylaminophenylazo]benzoic acid (DABCYL).

Raman amplifiers are also expected to be used globally as a key device in next-generation optical communications, for example, in wavelength-division-multiplexing (WDM) transmission systems. Raman scattering occurs when an atom absorbs a photon and another photon of a different energy is released. The energy difference excites the atom and causes it to release a photon with low energy; therefore, more light energy is transferred to the photons in the light path.

Improving the consistency of SERS probes requires the use of single, SERS active nano-sized structures. Nano-crescents, and core-shell systems are examples of cleverly engineered nanostructures capable of providing sufficient SERS intensity from individual particles due to their ability to strongly localize surface electromagnetic fields. (See in particular, Lu, Y., Liu, G. L., Kim, J., Mejia, Y. X., and Lee, L. P., Nano Lett. 2005, 5, 119-124; Talley, C. E., Jackson, J. B., Oubre, C., Grady, N. K., Hollars, C. W., Lane, S. M., Huser, T., Nordlander, P., and Halas, N. J., Nano Lett. 2005, 5, 1569-1574.) However, the relatively large size of these nanostructures will ultimately limit their accessibility to some subcellular organelles. To push the size boundary of sensing, as required by systems biology, even smaller probes will be required. Of interest is a subset of core-shell structures, hollow metal structures, a unique class of nanomaterials explored, most notably, by Sun et al. (Sun, Y. G., Mayers, B., and Xia, Y. N., Advanced Materials 2003, 15, 641-646). Utilizing the galvanic replacement of silver with gold and other metals, they have produced a variety of different sized and shaped hollow structures and have recently demonstrated the SERS activity of these structures (Chen, J. Y., Wiley, B., Li, Z. Y., Campbell, D., Saeki, F., Cang, H., Au, L., Lee, J., Li, X. D., and Xia, Y. N., Advanced Materials 2005, 17, 2255-2261).

In solid spherical particles there is a single resonance at approximately 520 nm for gold and 400 nm for silver, varying slightly depending on size and embedding media. However, when one axis is extended, for example, a nanorod, the resonance will break into two absorption bands, one corresponding to the short axis, or transverse mode, and another to the long axis, or longitudinal mode (Nikoobakht, B. and El-Sayed, M. A., Chem. Materials 2003, 15, 1957; Chang, S. S., Shih, C. W., Chen, C. D., Lai, W. C., and Wang, C. R. C., Langmuir 1999, 15, 701). The longitudinal mode has lower energy or redder absorption than the transfer mode. This is also true for aggregated systems in which there are multiple resonances within each given cluster of particles (Grant, C. D., Schwartzberg, A. M., Norman, T. J., and Zhang, J. Z., J. Am. Chem. Soc. 2003, 125, 549; Quinten, M. J., Cluster Sci. 1999, 10, 319; Quinten, M., Applied Physics B-Lasers and Optics 2000, 70, 579; Quinten, M. and Kreibig, U. Applied Optics 1993, 32, 6173; Norman, T. J. Jr. Grant, C. Magma, D. Cao, D. Bridges, F. Liu, J. van Buuren, T. and Zhang, J. Z., J. Phys. Chem. B 2002, 106, 7005; Norman, T. J., Grant, C. D., Schwartzberg, A. M., and Zhang, J. Z., Opt. Mat. 2005, 27, 1197; and Kreibig, U. Optical properties of metal clusters; Springer: Berlin; N.Y., 1995; Vol. 25). Therefore, controlling size and shape of these metal nanostructures allows control of their optical properties that have potential applications in nanophotonics and sensing.

As an effort to engineer so-called "hot spots" of large enhancement in single particles, Lee et al. produced nano-crescent structures by depositing silver over latex beads on a surface, then dissolving away the bead (Lu, Y., Liu, G. L., Kim, J., Mejia, Y. X., and Lee, L. P., Nano Lett. 2005, 5, 119). These hollow spheres are open-ended with a sharpened edge that greatly enhances the EM field. This engineered "hot-spot" approach yields improved SERS enhancements over core/shell systems and is of a similar homogeneity due to the highly consistent latex beads available. For applications requiring extremely small probe size, however, both nano-crescents and core shell systems are relatively large.

A system of particular interest where probe size is of utmost importance is intracellular studies (Chithrani, B. D., Ghazani, A. A., and Chan, W. C. W., Nano Lett. 2006, 6, 662-668). It has been found that while particles larger than 100 nm can enter a cell, they do not do so readily and may interrupt some cellular functions. Similarly, particles that are too small, less than 20 nm, will diffuse out of the cell, rendering them useless. The ideal is a structure that can be tuned in size between 20 nm and 100 nm depending on the application.

Nanotubes of all shapes and sizes have become an area of increasing interest for applications ranging from filtration to electrical interconnects. (See, in particular, Holt, J. K. et al., Science 312, 1034-1037 (2006); Hinds, B. J. et al., Science 303, 62-65 (2004); Zhang, M. et al. Science 309, 1215-1219 (2005); and Huang, Y. et al., Science 294, 1313-1317 (2001).) The application of these structures is almost unlimited, however, as is the case with most synthesized structures of this scale, nanoscopic manipulation is challenging. While carbon nanotubes have been the predominant structure of interest, lately there has been an effort to utilize gold and silver nanotubes or nanowires for these purposes as their conductivity and material properties are thought to be superior (Siwy, Z. et al., J. Am. Chem. Soc. 127, 5000-5001 (2005); Kohli, P., Wharton, J. E., Braide, O. & Martin, C. R. J., Nanosci. Nanotechnol. 4, 605-610 (2004)). Generally these metal structures are produced by a physical or electroless deposition technique, and while this produces well defined structures, their shape and size is entirely dependent on the template on which they are made, limiting the size and practical application of these structures (Wiley, B., Sun, Y. G., Mayers, B. & Xia, Y. N., Chemistry-a European Journal 11, 454-463 (2005); Wiley, B. et al., M. R. S. Bull., 30, 356-361 (2005); Sun, Y. G. & Xia, Y. N. Advanced Materials 16, 264-268 (2004); and Lee, M., Hong, S. C. & Kim, D., Appl. Phys. Lett., 89 (2006)).

There is therefore a need in the art for use in the chemical and biomedical analytical industries and the electronic communications industries to provide more sensitive compositions and devices that are inexpensive to manufacture and easy to use.

BRIEF DESCRIPTION OF THE INVENTION

The present invention provides nanostructures comprising hollow metal nanospheres or nanoshells and nanotubes for use as chemical sensors, conduits for fluids, and electronic conductors. The nanostructures can be used in microfluidic devices, for detecting chemicals inside or outside a biological membrane, such as a cell membrane or a viral coat, for transporting fluids between devices and structures in analytical devices, for conducting electrical currents between devices and structure in analytical devices, and for conducting electrical currents between biological molecules and electronic devices, such as microchips.

In one embodiment the present invention provides a chemical sensor comprising gold nanoshells (hollow gold nanospheres; HGN), the nanoshells having a mean particle size of between about 20 nm and about 100 nm diameter. In one preferred embodiment the mean diameter is between about 20 nm to about 70 nm. In another preferred embodiment, the mean diameter is between about 22.8 nm and about 50 nm diameter. In one embodiment, the invention provides a chemical sensor for chemical and biological sensing applications, particularly those requiring near-IR absorption.

The HGNs have an interior wall surface diameter and an exterior wall surface diameter thereby defining the wall thickness. The invention further provides HGNs having tunable interior and exterior and wherein the peak of the surface plasmon band absorption is between about 550 nm and about 820 nm. In one embodiment the mean wall thickness of the HGNs is between about 2.4 nm and about 7.3 nm. In a preferred embodiment the mean wall thickness is about 5 nm.

In another preferred embodiment, the chemical sensor has a surface wherein the surface can induce surface enhanced Raman scattering (SERS).

In still another preferred embodiment, the chemical sensor further comprises at least one detecting molecule, wherein the detecting molecule is bound to the surface. In a more preferred embodiment the detecting molecule is selected from the group consisting of proteins, peptides, antibodies, antigens, nucleic acids, peptide nucleic acids, sugars, lipids, glycophosphoinositols, and lipopolysaccharides.

In a yet more preferred embodiment the detecting molecule is an antibody. In another preferred embodiment, the detecting molecule is an antigen.

In another embodiment, the invention provides a chemical sensor further comprising at least one semiconductor quantum dot. In a preferred embodiment the semiconductor quantum dot further comprises a linker molecule, the linker molecule selected from the group consisting of a thiol group, a sulfide group, a phosphate group, a sulfate group, a cyano group, a piperidine group, an Fmoc group, and a Boc group.

In a still further embodiment, the invention provides a chemical sensor comprising at least one semiconductor quantum dot wherein the semiconductor quantum dot further comprises a detecting molecule, wherein the detecting molecule is bound to the semiconductor quantum dot. In a more preferred embodiment, the detecting molecule is selected from the group consisting of proteins, peptides, antibodies, antigens, nucleic acids, peptide nucleic acids, sugars, lipids, glycophosphoinositols, and lipopolysaccharides.

In a more preferred embodiment, the detecting molecule is an antibody. In the alternative, a more preferred embodiment comprises a chemical sensing device wherein the detecting molecule is an antigen.

Another embodiment of the invention provides a method for detecting an analyte in a sample using a chemical sensor, the method comprising the steps of: i) providing a sample; ii) providing a semiconductor quantum dot comprising a linker molecule (LM-SQD); iii) conjugating the analyte in the sample with the LM-SQD thereby producing an analyte-LM-SQD conjugate; iv) providing a chemical sensor comprising a plurality of particles, each particle comprising: a shell having at least one surface and wherein the shell comprises a gold molecular species, the shell surface further comprising a detecting molecule; v) incubating the analyte-LM-SQD conjugate with the chemical sensor for a predetermined time period; and vi) measuring the extent of binding between the analyte-LM-SQD conjugate and the chemical sensor; thereby detecting the analyte in the sample. In one embodiment the sample is selected from the group consisting of mammalian cells, vertebrate cells, invertebrate cells, plant cells, fungal cells, mold cells, archaeal cells, bacterial cells, viruses, bacteriophages, and the like. In another embodiment the sample is selected from the group consisting of blood fluids, lymph fluids, hemolymph fluids, pulmonary surfactant fluids, peritoneal fluids, gastric fluids, xylem fluids, phloem fluids, and the like. In yet another embodiment the sample is selected from the group consisting of fluvial fluids, marine fluids, atmospheric precipitate fluids, waste-water fluids, agricultural run-off fluids, fluids comprising hydrocarbons, fluids contaminated by hydrocarbons, aerosol fluids, aqueous fluids, non-aqueous fluids, and the like.

The invention also provides a method of using the chemical sensor as disclosed herein for measuring cellular processes. These embodiments are merely exemplary of the invention, which encompasses any small nanostructures having SERS activity as disclosed herein.

In another embodiment the invention provides a method for detecting an analyte that is a cancer marker. In one embodiment the cancer marker is an antibody. In one embodiment of the invention the detecting molecule in the chemical sensor is an antigen that binds to a cancer marker antibody with an affinity ($K_a$) of at least $10^6$ l/mole. In a more preferred embodiment the $K_a$ is at least $10^8$ l/mole. In another preferred embodiment the analyte is a phospholipid. In a most preferred embodiment the phospholipid is lysophosphatidic acid (LPA).

The invention further provides a synthetic nanotube, the synthetic nanotube being substantially hollow and having dimensions of between about 20 nm and about 100 nm in mean diameter and at least between about 0.1 µm and 4 µm in mean length. In a more preferred embodiment the mean diameter is between about 30 nm and 80 nm. In a more preferred embodiment the mean length is between about 4 µm and about 50 µm, for example, about 6 µm, about 8 µm, about 10 µm, about 15 µm, about 20 µm, about 25 µm, about 30 µm, about 40 µm, and about 50 µm, and any other length therebetween.

In one embodiment the synthetic nanotube has a wall of mean dimension of between about 2.4 nm and about 7.3 nm across. In a preferred embodiment the wall has a mean dimension of about 5 nm.

In one preferred embodiment the synthetic nanotube comprises a metal selected from the group consisting of gold, silver, platinum, copper, aluminum, palladium, cadmium, iridium, rhodium, and the like.

In another embodiment, the invention provides a conduit for conducting fluids, the conduit comprising the synthetic nanotube as disclosed herein.

In yet another embodiment, the invention provides an electronic conductor, the electronic conductor comprising the synthetic nanotube as disclosed herein.

The invention further provides a method for synthesizing a nanotube, the nanotube comprising a metal, the method comprising the steps of (i) combining an aqueous solution of $Co^{2+}$ salt with an aqueous solution of citrate salt thereby forming a first mixture (ii) degassing the first mixture; (iii) purging at least once with nitrogen gas; (iv) adding an aqueous solution of $NaBH_4$ thereby reducing the $Co^{2+}$ to $Co^0$, and thereby forming a second mixture comprising $Co^0$ particles, the step of adding being in the presence of an induced magnetic field and wherein the presence of the induced magnetic filed aligns the $Co^0$ particles; (v) agitating the second mixture until hydrogen evolution is substantially complete; (vi) adding the second mixture comprising aligned $Co^0$ particles to an aqueous solution of $Au^{3+}$ salt; (vii) allowing the $Au^{3+}$ to be reduced to $Au^0$ and the $Co^0$ oxidized to $Co^{2+}$, and wherein the $Au^0$ is deposited adjacent to the aligned $Co^0$ thereby creating a nanotube comprising $Au^0$, the method thereby synthesizing a nanotube. In one preferred embodiment the nanotube comprises a metal selected from the group consisting of gold, silver, platinum, copper, aluminum, palladium, cadmium, iridium, and rhodium.

BRIEF DESCRIPTION OF THE DRAWINGS

FIG. 13A is a high resolution TEM of a single, 30 nm HGN. The wall thickness is approximately 4 nm and large areas of crystallinity are clearly visible. FIGS. 13B-E are low resolution TEM images of particles of 71±17 nm (B), 50±5 nm (C), 40±3.5 nm (D), and 28±2.3 nm.

FIG. 20a is a low resolution TEM image of gold nanotubes. Red line indicates the path of a single ~4 mm tube. FIG. 20b is a high resolution TEM image of a large section of one tube illustrating the continuity and consistency of the samples. FIG. 20c is a high resolution TEM image of one section of the gold tube showing its continuous nature. FIG. 20d is a more detailed high resolution TEM image of the tube showing gold lattice fringes indicating its poly-crystalline nature.

DETAILED DESCRIPTION OF THE INVENTION

Figure 1:
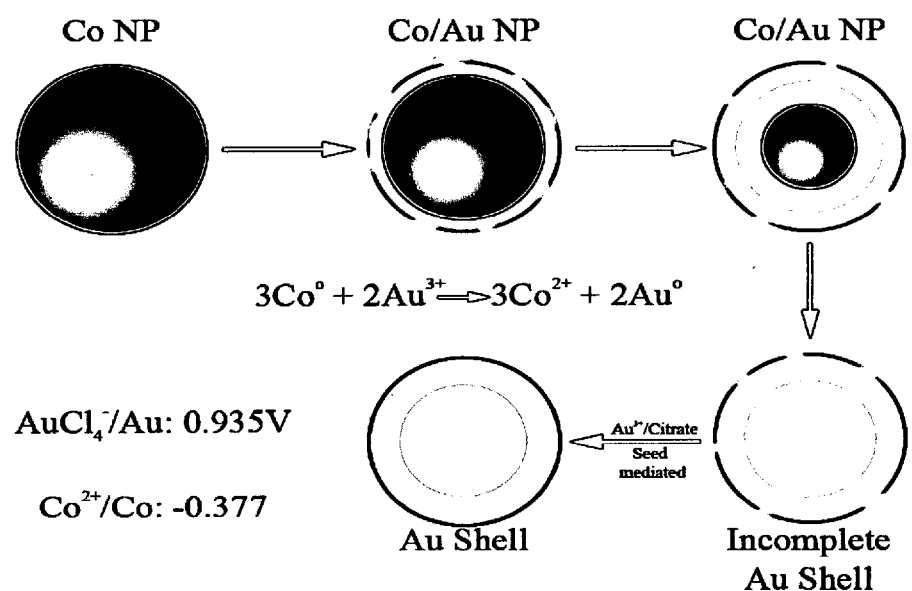
FIG. 1 shows an exemplary synthesis procedure for HGNs.

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a particle" includes a plurality of such particles, and a reference to "a surface" is a reference to one or more surfaces and equivalents thereof, and so forth.

The invention disclosed herein is based on the galvanic replacement of cobalt with gold, a procedure shown to produce considerably more homogeneous hollow spheres than those synthesized with silver (Liang, H. P.; Wan, L. J.; Bai, C. L.; Jiang, L. J., Phys. Chem. B 2005, 109, 7795-7800). The process starts with a cobalt nanoparticle that is synthesized as a template for the growth of hollow gold nanospheres (HGNs). Utilizing the difference in redox potential between cobalt and gold, it is possible to reduce gold ions while oxidizing the cobalt nanoparticles. Because this reaction takes place entirely at the surface of the cobalt particle, the shape and size of the resulting hollow structure is completely dependent on the original template. Moreover, this process is able to produce SERS active nanoparticles that are significantly smaller than traditional nanoparticle structures used for SERS, providing a sensor element that can be more easily incorporated into cells for localized intracellular measurements.

We provide the successful SERS application of HGNs with improved optical and structural homogeneity over other SERS substrates that are highly desired and important for size sensitive biological sensing applications. The consistency of particle shape and size is reflected in the optical properties that lead to a tenfold increase in SERS spectral consistency over aggregated silver nanoparticles commonly used in SERS applications. SERS from single HGNs was achieved, the first such measurement on hollow nanostructures. Finally, pH sensing as a model system was demonstrated showing an approximate doubling of resolution and a ten-fold increase in precision over previous nano-sized pH SERS probes. This clearly represents a new detecting platform and a major step forward in potential biological sensing applications.

Since the early work by Turkevich et al. and later Frens et al., it has been understood that in a standard colloidal gold synthesis using the hot citrate reduction of chloroauric acid, the particle size may be controlled by the concentration of citrate. Citrate stabilizes the initially formed nuclei and the more citrate is present, the more nuclei will be stabilized. However, when trying to apply this logic to the aqueous synthesis of cobalt nanoparticles, it is a significantly more challenging task. (See Turkevich, J.; Stevenson, P. C.; Hiller, J., Discussions of the Faraday Society 1951, 11, 55; Frens, G., Nature Physical Science 1973, 241, 20.)

Due to the stability of the cobalt salt, the reduction cannot be done by citrate alone and a stronger reducing agent is required. In this case sodium borohydride is used to reduce the salt, and citrate is present only as a capping agent.

Nearly monodisperse HGNs with tunable interior and exterior diameter have been synthesized by sacrificial galvanic replacement of cobalt nanoparticles. By carefully controlling particle size and wall thickness, it is possible to tune the peak of the surface plasmon band absorption between 550 nm and 820 nm. Cobalt particle size is tunable by simultaneously changing the concentration of sodium borohydride and sodium citrate, the reducing and capping agent, respectively. The thickness of the gold shell can be varied by carefully controlling the addition of gold salt. With successful demonstration of ensemble as well as single HGN surface enhanced Raman scattering, these HGNs have shown great potential for chemical and biological sensing applications, especially those requiring nanostructures with near IR absorption.

In this application we present the synthetic route necessary to control the particle size of the cobalt nanoparticles, which is reflected in the resultant HGN diameter. The inner diameter, or wall thickness, can be controlled by the concentration of gold salt used, leading to complete control of the optical properties of particles ranging from 20 nm to 70 nm. For a particular diameter and wall thickness, the absorption band is relatively narrow due to the near monodisperse distribution, as determined by single nanosphere scattering spectrum. These HGNs have been further demonstrated to be excellent SERS substrates with excellent consistency measured based on single HGN SERS spectrum.

The size of the particles can be in the range from between about 20 nm to about 100 nm, about 25 nm to about 85 nm, about 35 nm to about 70 nm, and about 50 nm in diameter. The dimensions of the wall of the particle, that is the wall thickness, is in the range form about 2.4 nm to about 10 nm, from about 2.4 nm to about 7.3 nm, and about 5 nm thick.

Figure 2:
FIG. 2 illustrates the different tunable colors of the HGNs having combinations of different dimensions.
Figure 3:
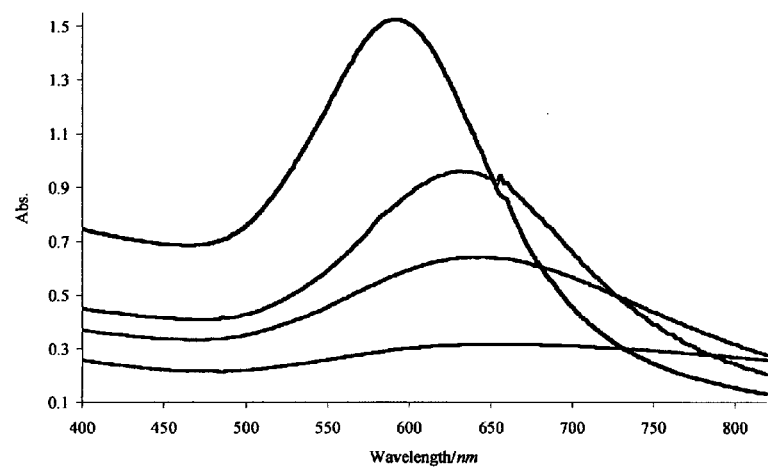
FIG. 3 illustrates the UV-visible electronic absorption spectra of different HGNs.
Figure 5:
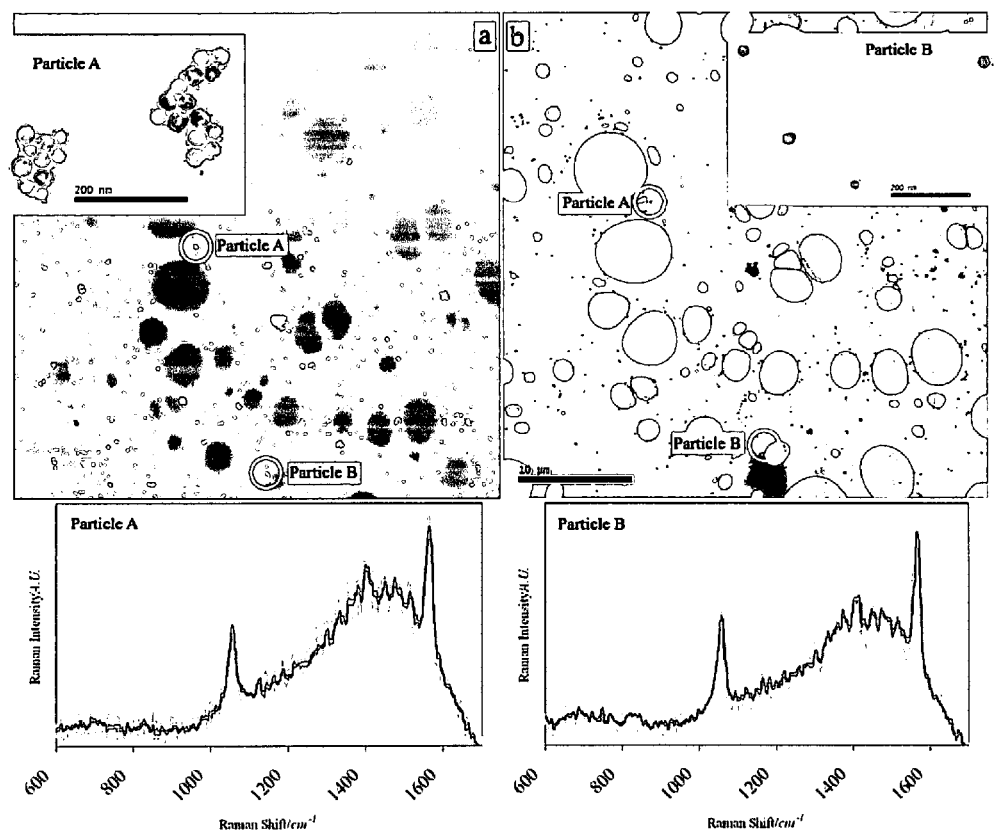
FIG. 5 illustrates a correlation between confocal SERS (a) and TEM (b).

An exemplary method for synthesizing HGNs is illustrated on FIG. 1. FIG. 2 illustrates the different color spectra associated with HGNs of different combinations of shell thickness and outer shell diameter. FIG. 3 exemplifies the UV-visible electronic absorption spectra of HGNs having a variety of combinations of shell thickness and outer diameter FIG. 5 compares a confocal image (labeled a) with that of a TEM (labeled b) of a sample of nanospheres. The inset photomicrographs show a high resolution image of Particle A and of Particle B; the graphs below show the SERS spectrum associated with Particle A or Particle B which can be discretely distinguished. As used herein, the terms "nanoshells" and "hollow nanospheres" are interchangeable.

SERS Detection Applications for Sensing and Imaging

Raman spectroscopy is a powerful optical technique for detecting and analyzing molecules. Its principle is based on detecting light scattered off a molecule that is shifted in energy with respect to the incident light. The shift, called Raman shift, is characteristic of individual molecules, reflecting their vibrational frequencies that are like figure prints of molecules. As a result, the key advantage of Raman spectroscopy is its molecular specificity while its main limitation is the small signal due to low quantum yield of Raman scattering. One way to enhance the Raman signal is to tune the excitation wavelength to be on resonance with an electronic transition, so called resonance Raman scattering. This can usually produce an enhancement on the order of $10^2$-$10^3$. Another technique to enhance Raman scattering is surface enhancement by roughened metal surfaces, notably silver and gold, that provides an enhancement factor on the order of $10^6$-$10^8$. Similar or somewhat larger enhancement factors ($\sim 10^8$-$10^{10}$) have been observed for metal, mostly silver, nanoparticles.

In the last few years, it has been shown that an even larger enhancement (~$10^{10}$-$10^{15}$) is possible for aggregates of metal nanoparticles, for example, comprising silver and/or gold. The largest enhancement factor of $10^{14}$-$10^{15}$ has been reported for rhodamine 6G (R6G) on single silver nanoparticle aggregates. This huge enhancement is thought to be mainly due to significant enhancement of the local electromagnetic fields of the nanoparticle aggregates that absorb strongly the incident excitation light for the Raman scattering process. With such large enhancement, many important molecules that are difficult to detect with Raman normally can now be easily detected. This provides many interesting and new opportunities for detecting and analyzing molecules using SERS with extremely high sensitivity and molecular specificity.

SERS can also be developed into a molecular imaging technique for biomedical and other applications. Exciting Raman imaging equipment may be usable for SERS imaging. SERS can provide an enhanced signal and thereby significantly shortened data acquisition time, making the technique practically useful for medical or other commercial and industrial applications including, but not limited to, chip inspection or chemical monitoring.

Antigen/Antibody Detection with Metal and Semiconducting Nanoparticles

Fluorescent nanoparticles (semiconductor quantum dots, SQDs) have been used recently as fluorescent biological markers and have been found to be extremely effective. They offer advantages including higher stability, stronger fluorescence, tunability of color, and possibility of optical encoding based on different sized or colored SQDs.

HGNs of the invention can be used to detect an analyte. Such an analyte can be, for example, but not limited to, an antigen, an antibody, a biochemical metabolite, an organic compound, a compound or element having biological activity, or the like.

SERS is also useful for detecting other cancer biomarkers that can interact or bind to the HGN surface. For example, Sutphen et al. have recently shown that lysophospholipids (LPL) are potential biomarkers of ovarian cancer (Sutphen et al., (2004) Cancer Epidemiol. Biomarker Prev., 13: 1185-1191). Based on the molecular structure of LPL molecules, a favorable interaction between LPL molecules with HGN through electrostatic interaction can occur at the appropriate pH. In the case of the SERS experiment using a polyclonal Ab, the strongest interaction with HGN occurs at the isoelectrostatic pH, i.e. pH at which the HGN has equal number of positive and negative charges. The pH is varied to adjust the charge on the HGN to determine the optimal pH or charge for strong interaction with LPL.

By conjugating fluorescent nanoparticle QDs to antigens and mixing the Ag-QD conjugate with a HGN-Ab composition, quenching of fluorescence upon binding of the antigen/antibody pair can be observed. The Ag and/or the Ab can be conjugated to the QD or HGN using a linker molecule (LM). A decrease in fluorescence can indicate the presence of the antibody for that particular antigen to which the fluorescing QDs have been attached. Depending on which antigen is utilized a wide array of antibodies can be detected. This can allow for the rapid detection of cancers or diseases that currently can take days or weeks to diagnose. Likewise, the scheme can work as well if antibody is attached to a fluorescent QD and the respective antigen to a metal nanoparticle. Metal particles have no florescence with visible excitation. The fluorescence quenching by metal nanoparticles can be more effective than quenching by larger QDs. This approach is sensitive and specific. The distance between the metal nanoparticle and QD is important for this to work (for example, the distance can be less than 2 nm). The interaction between the two components can be adjusted to achieve the maximum quenching effect.

Detection of Tumor Markers

Surface-enhanced Raman scattering using silver nanoparticles was applied to detect various forms of lysophosphatidic acid (LPA) to examine its potential application as an alternative to current detection methods of LPA as biomarkers of ovarian cancer. Enhancement of the Raman modes of the molecule, especially those related to the acyl chain within the 800-1300 cm$^{-1}$ region, was observed. In particular, the C—C vibration mode of the gauche-bonded chain around 1100 cm$^{-1}$ was enhanced to allow the discrimination of two similar LPA molecules. Given the molecular selectivity of this technique, the detection of LPA using SERS may eliminate the need for partial purification of samples prior to analysis in cancer screening.

Lysophosphatidic acid (LPA), originally known for its role as an intermediate in intracellular lipid metabolism, has now been recognized as an important multifunctional biological mediator that can elicit cellular responses including mitogenic and antimitogenic effects on the cell cycle, actin skeleton regulation, and cellular motility (see Tigyi et al., (1994) Proc. Nat. Acad. Sci. 91: 1908-1912; van Corven et al., (1989) Cell 59: 45-54; Ridley and Hall, (1992) Cell 70: 389-399; and Zhou et al., (1995) J. Biol. Chem. 270: 25549-25556). The involvement of LPA in inducing cell proliferation, migration and survival implicates it in the initiation and progression of malignant disease, and has been proposed as a sensitive biomarker for ovarian cancer (see Xu et al. (1998) JAMA 280: 719-723; Mills and Moolenaar (2003) Nature Rev. 3: 582-591; Fang et al. (2004) J. Biol. Chem. 279: 9653-9661; and Sutphen et al. (2004) Cancer Epidemiol. Biomark. Prev. 13: 1185-1191).

Typically, the detection of LPA has been conducted using chromatography and mass spectroscopy assays that require a partial purification of the samples using thin layer chromatography (TLC) prior to analysis. Although this method is effective, an underestimation of LPA concentration can result during the recovery process due in part to the varying mobility of the LPA salts (free acid, sodium and calcium salts) when subjected to chromatography by TLC. The low stability of LPA also calls for fast and sensitive detection techniques.

A powerful optical detection technique based on surface-enhanced Raman scattering (SERS) offers a unique combination of high sensitivity and molecular specificity. With SERS, the Raman signal of a molecule is increased by many orders of magnitude as a result of strong enhancement of the excitation light through the resonance of the metal's surface electrons called the surface plasmon (see Moskovits (1985) Rev. Modern Physics 57: 783-828; Otto et al., (1992) J. Phys. Condense Matter 4: 1143-1212; and Campion and Kambhampati, (1998) Chem. Soc. Rev. 27: 241-250). SERS has been successfully used in the detection and analysis of a large number of chemicals and biological molecules (see Albrecht and Creighton, (1977) J. Am. Chem. Soc. 99: 5215-5217; Nie and Emory (1997) Science 275: 1102-1106; Keating et al., (1998) J. Phys. Chem. B 102: 9414-9425; Kneipp et al., (1998) Phys. Rev. E 57: R6281-R6284; and Schwartzberg et al., (2004) J. Phys. Chem. B 108: 19191-19197).

SERS Application for Detection and Analysis of Semiconductor Nanoparticles

Another application of SERS based on the gold nanoparticle system is for measuring Raman spectrum of semiconductor nanoparticles (QDs). Similar to molecules, normal Raman signals are very small and thus Raman spectrum is challenging to measure. SERS as an enhanced Raman technique for measuring Raman for semiconductor nanoparticles have not been reported before. The surface chemistry of the metal nanoparticles and the semiconductor QDs must be compatible for this to work. The sulfur species on the surface of the HGNs are ideal for II-VI SQDs to bind, enabling SERS detection of the SQDs. This provides a powerful method for detecting and analyzing semiconductor nanoparticles.

The material and methods described heretofore have additional properties and uses. As such, we herein disclose an aqueous solution phase synthesis of continuous gold nanotubes that are controllable in shape and size, currently up to 5 mm in length, by magnetic field manipulation and synthetic parameters. Because of the ease with which magnetic fields may be manipulated, precise placement should not only be possible, but relatively simple as compared to other methods. This is the first step in producing controllable, well-defined, chemically stable structures for any application that requires hollow, electrically conducting one-dimensional nanomaterials.

Use of Nanostructures in Miniature Electrical Circuits

The nanostructures in the form of nanotubes can be used in the production of miniature electronic circuits, with applications in the microelectronics industries for producing very small circuits for memory chips, for creating electrical circuits used with biological media, such as proteins, including cell surface receptor proteins, antibodies; photosensitive compounds, such as chlorophyll and related compounds; xanthocyanins; compounds having oxidoreductase activity, including, but not limited to, cytochromes and related compounds, haemoglobin, myoglobin, and the like, and fluorescent compounds.

Synthesis of Nanotubes using Magnetic Alignment of Metal Particles

In previous works we and others have shown that it is possible to produce highly uniform hollow gold nanospheres (HGN) using synthesized cobalt nanoparticles in aqueous solution as sacrificial electroless deposition templates (Schwartzberg, A. M., Olson, T. Y., Talley, C. E. and Zhang, J. Z. J. Phys. Chem. B 110, 19935-19944 (2006)). In this reaction $Au^{3+}$ is reduced to $Au^0$ by $Co^0$ nanoparticles via the following mechanism:

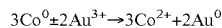

Because only two gold atoms are generated for every three cobalt atoms oxidized, there is a net loss of volume, resulting in gold nanostructures of approximately ⅔ the volume of the original Co nanoparticle. Since the gold shell grows inward from the surface of the cobalt particle, a void remains at the center of the final gold nanostructure that is filled, most likely, by water and various ionic species. The shape and size of these hollow structures therefore depends strongly on the original cobalt nanostructure.

We have found that the size and shell thickness of HGNs can be rather simply controlled by synthetic methods (Schwatzberg (2006) supra). In attempts to increase particle size, and thereby red-shift the resulting HGN plasmon into the near IR, it was found that reducing the concentration of sodium citrate, the particle stabilizing agent, and increasing the concentration of the cobalt salt results in a controllable aggregation of the cobalt nanoparticles. By carefully varying the citrate concentration we were able to induce varying states of aggregation from complete flocculation to partial crosslinking. Surprisingly, in the presence of a relatively strong magnetic field, a magnetic stir-plate or the like, upon reaction with the gold salt, these weakly aggregated cobalt nanoparticles were found to produce long, well organized gold tubes as in FIG. 20a. While the alignment of cobalt nanoparticles has been observed in the past, this is the first time the phenomenon has been used to create extended gold nanostructures (Puntes, V. F., Krishnan, K. M. and Alivisatos, A. P., Science 291, 2115-2117 (2001); Salgueirino-Maceira, V. and Correa-Duarte, M. A., J. Mat. Chem. 16, 3593-3597 (2006); and Salgueirino-Maceira, V., Correa-Duarte, M. A., Hucht, A. and Farle, M., J. Magnetism Magnet. Mat. 303, 163-166 (2006)).

Such a surprising occurrence would not have been predicted and is clearly an example of superior unexpected results when compared with what is known in the prior art.

Figure 20:
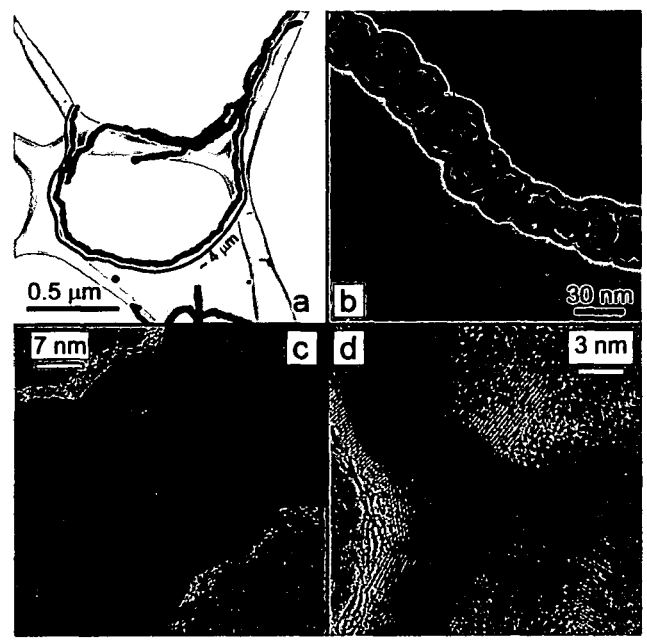
FIG. 20 illustrates TEMs of the gold nanotubes.

The highlighted tube in FIG. 20a is over 4 μm long and upon close inspection, the location of each individual cobalt particle that oxidized to form the gold tube is clear. This leads to the almost peapod or intestine-like structure of the tube and it is clear that the cobalt particles are aligning into a "string of pearls" type structure. From low resolution TEM images it is not entirely clear if each section of the "intestine" is divided by walls, or if the hollow portion of the tube is continuous. High resolution TEM, however, conclusively shows that in most cases the whole tube is hollow and polycrystalline in nature, that is, nanotubes, not rods or wires (see FIGS. 20b, c, and d). We thought initially that these may be aggregates of gold nanoshells, which would be easier to explain. However, closer examination by HRTEM shows that this is not the case since the hollow part of the structure is connected throughout the whole tube (FIGS. 20b and c) and the lattice fringes of each "section" extend into the next indicating simultaneous growth (FIG. 20d). Therefore, the nanotube structure is clearly not simply aggregates of gold nanoshells. Furthermore, the apparent one-dimensional (or linear) structure is inconsistent with randomly aggregated structures that tend to be three-dimensional. The linear structure suggests that something is directing the formation of the nanotube structure in an ordered manner.

Figure 21:
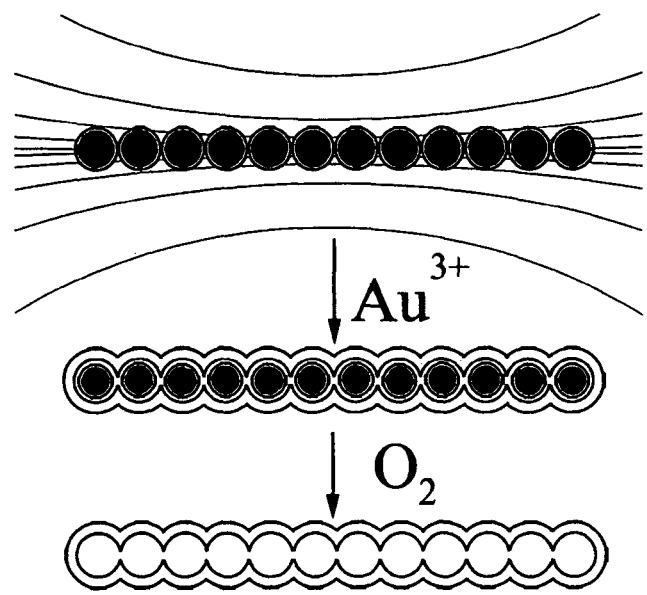
FIG. 21 is a schematic of gold tube formation templated with Co nanoparticles aligned by an external magnetic field. Top portion of figure: alignment of cobalt nanoparticles along magnetic field lines. Middle portion: Gold is reduced onto the surface of aligned cobalt particles. Bottom portion: Cobalt is further oxidized by dissolved oxygen leaving a hollow structure.

One possible clue to explaining the formation of the Au nanotubes comes from the magnetic property of the seeding Co nanoparticles and the application of an external magnetic field to drive a magnetic stir bar during synthesis. To test this, we then intentionally examined the effect of an external magnetic field on the synthesis process and the final product. We have found that the magnetic field has a strong influence on the formation of the nanotubes. Without an external magnetic field we observed little or no nanotube formation. This led us to suggest that the mechanism of growth depends on the ordering of the Co nanoparticles by a magnetic field. The initial finding of nanotubes was the result of an unintended use of a magnetic stir bar and plate that uses a strong magnetic field that caused alignment of the Co nanoparticles. Even though Co nanoparticles are magnetic and could align by themselves, this self-alignment is apparently insignificant at room temperature. When the magnetic field is strong enough, the Co nanoparticles align into chains along the field lines by the applied external magnetic field, as illustrated in FIG. 21. Reduction of Au salt into Au metal with these aligned Co chains resulted in the formation of the Au nanotube. The Co nanoparticles are close enough that the Au salt cannot access the interstitial space between the particles resulting in a structure with a completely hollow core.

It is possible not only to control the cobalt particle before reacting with gold. By performing the reaction in an oxygen free environment and using only enough gold to oxidize part of the cobalt particles, we were able to leave some portion of the magnetic particles at the core of the gold tube. The tube is then magnetically controllable and can be aligned in whatever way desired by magnetic field manipulation. By merely exposing the tubes to oxygen, the cobalt was completely oxidized within seconds and dissolved into solution, leaving a completely hollow tube.

Given the nature of the tube synthesis there are always pores that allow gold ions to permeate in to react with the cobalt and to allow oxidized cobalt to diffuse out. It is important to note that for applications requiring pore free tubes, it is simple to backfill the holes after the oxidation of cobalt is complete. By adding additional gold salt in the presence of sodium citrate, a seed mediated growth mechanism will induce reduction of gold at the tube surface, specifically at sharp features such as pores. With this process it is possible to form smooth surfaced tubes and, with sufficient gold salt, grow the wall thicker if desired. The potential applications of this type of controllable, conducting nanostructure are numerous.

In addition, we have found that the average length of the tubes is dependent on the amount of initial cobalt aggregation chemically induced. By decreasing the amount of sodium citrate it is possible to lengthen the tubes. With this, we have additional control of the structures. Length and diameter can be controlled chemically, wall thickness can be controlled by the amount of gold added, and order and placement can be controlled magnetically. It should be noted that tubes are not formed when sufficient citrate is present to prevent aggregation. This indicates that, while the particles may align in the presence of the magnetic field, they are not close enough to prevent the Au salt from penetrating the junction of the particles to reduce at their surfaces. The synthesis has been reproduced by different researchers in our lab independently with very similar results. The electromagnetic field can be generated, for example, using a magnetic stirbar and a rotating magnet system well-known to those of skill in the art. In addition, an electromagnetic field can be induced using a generator or the like that induces an electromagnetic filed in the vicinity of the experimental particles to be aligned. Other physical means for inducing an electromagnetic field are well-known to those of skill in the art.

Figure 22:
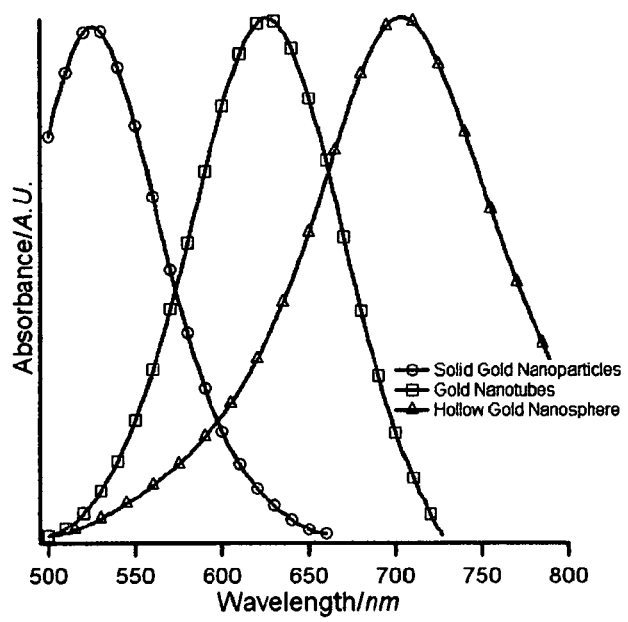
FIG. 22 illustrates the UV-visible absorption spectra of 50 nm diameter solid gold nanoparticle solution, 40 nm diameter nanotube with ~5 nm shell thickness solution, and 60 nm diameter HGN with 3 nm shell thickness solution.
Figure 23:
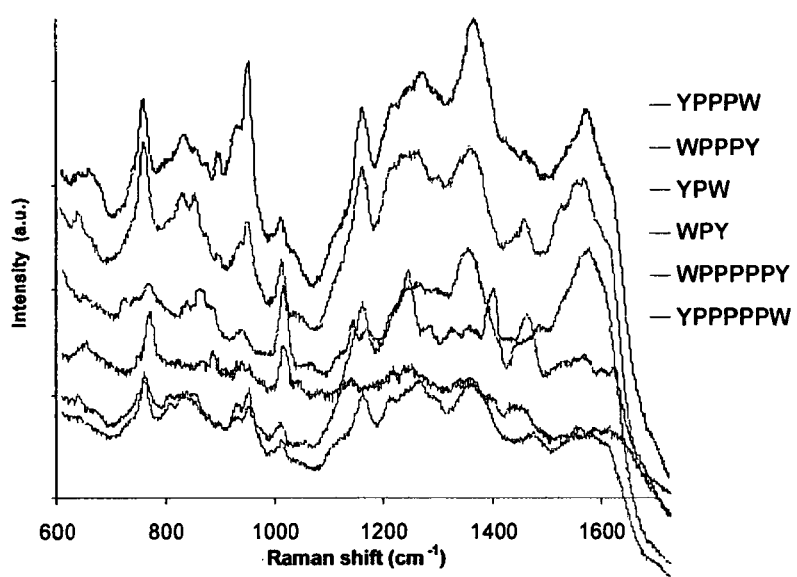
FIG. 23 illustrates how the terminal amino acid residues in different peptides affect the SERS spectrum. The SERS spectra change when the terminal amino acid residue is changed thereby indicating a possible relationship between SERS spectrum and distance between the terminal residues. Y=tyrosine; P=proline, and W=tryptophan.
Figure 24:
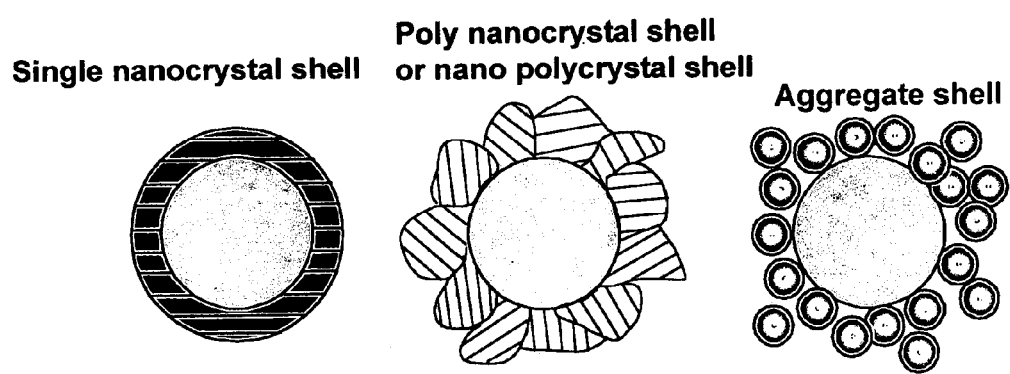
FIG. 24 illustrates cross-sectional representations different hollow nanosphere or nanoshell structures. The same structures can be considered for nanotubes in cross-section.

Associated with the novel Au nanotubular structure are some interesting optical properties. Generally, gold nanostructures with asymmetric axes, such as nanorods, will exhibit multiple plasmon absorption bands. A red shifted longitudinal band and a transverse band to the blue associated with the long axis and the short axis of the structure, respectively. A third mode perpendicular to the wall of the tube is likely too blue to be observed due to the thinness of the wall. In the absorption spectra of these structures, however, there is only one band despite the presence of two possible axes of plasmon oscillation (FIG. 22). There are two possible explanations for this. First, because of their length, the longitudinal mode is red shifted far into the near IR and is not visible in the range in which we are looking. More likely, however, there is no surface plasmon absorption observed on the long axis because it is on the micron length scale and any electron oscillation is no longer surface confined and is more bulk-like. Therefore, the absorption peak present in FIG. 22 must be due to oscillations around the circumference of the tube only. This is further reinforced by the spectral position of the nanotube band between the thinly shelled 60 nm HGNs and solid gold nanoparticles. With an average diameter of 40 nm and wall thickness of ~5 nm the circumference of the tube should yield a plasmon absorption red shifted from the HGN presented.

The mean length of the nanotube can be, for example, between about 0.1 μm and about 50 μm, such as 0.1 μm, 0.2 μm, 0.5 μm, 0.75 μm, 1.0 μm, 1.5 μm, 2.0 μm, 3.0 μm, 4.0 μm, 5.0 μm, 7.5 μm, 10 μm, 15 μm, 20 μm, 25 μm, 30 μm, 35 μm, 40 μm, 45 μm, 50 μm, or any length therebetween. The length can be measured using electron microscopy and standard metrics well known to those of skill in the art. The mean wall thickness can be, for example, 0.5 nm. 1.0 nm, 1.5 nm, 2.0 nm, 2.4 nm, 2.6 nm, 3.0 nm, 4 nm, 5 nm, 6 nm, 7 nm, 7.3 nm, 8 nm, 9 nm, and 10 nm, or any thickness therebetween The mean diameter of the nanotube can be, for example, 10 nm, 20 nm, 30 nm, 40 nm, 50 nm, 60 nm, 70 nm, 80 nm, 90 nm, and 100 nm, or any diameter therebetween. The mean diameter can be measured from the image on an electronmicrograph. The mean diameter can be measured over a portion of the entire nanotube.

In summary, we herein present a new method for producing chemically stable and electrically conducting nanotubes. The length, diameter, and wall thickness of the nanotubes can be controlled chemically while their position and structural alignment can be controlled magnetically. This method affords the possibility of fabricating a variety of easily manipulated, useful linear nanotubular structures for different applications.

Synthesis of Biological Molecules
Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker molecule. A linker molecule such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin.

Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full-length peptide is synthesized by sequential deprotection, coupling of derivatized amino acids, and washing with dichloromethane and/or N,N-dimethylformamide. The peptide is cleaved between the peptide carboxy terminus and the linker group to yield a peptide acid or amide. These processes are described in the Novabiochem 1997/98 Catalog and Peptide Synthesis Handbook (San Diego Calif. pp. S1-S20). Automated synthesis may also be carried out on machines such as the ABI 431A peptide synthesizer (ABI). A protein or portion thereof may be purified by preparative high performance liquid chromatography and its composition confirmed by amino acid analysis or by sequencing (Creighton (1984) Proteins, Structures and Molecular Properties, WH Freeman, New York N.Y.).

In particular, a purified antigen may be used to produce antibodies or to screen libraries of pharmaceutical agents to identify those that specifically bind an antigen. Antibodies to an antigen may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with an antigen or with any fragment or oligopeptide thereof that has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemacyanin (KLH), and dinitrophenol. Among adjuvants used in humans, BCG (bacilli Calmette-Guerin) and *Corynebacterium parvum* are especially preferable. (For review of methods for antibody production and analysis, see, for example, Harlow and Lane (1988) Antibodies: A Laboratory Manual, Cold Spring Harbor Laboratory, Cold Spring Harbor, N.Y.)

It is preferred that the oligopeptides, peptides, or fragments used to induce antibodies to an antigen have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of antigen amino acids may be fused with those of another protein, such as KLH, and antibodies to the chimeric molecule may be produced.

Antibodies

Monoclonal antibodies to an antigen may be prepared using any technique that provides for the production of antibody molecules by continuous cell lines in culture. These include, but are not limited to, the hybridoma technique, the human B-cell hybridoma technique, and the EBV-hybridoma technique. (See, for example, Kohler et al. (1975) Nature 256: 495-497; Kozbor et al. (1985) J. Immunol. Methods 81: 31-42; Cote et al. (1983) Proc. Natl. Acad. Sci. 80: 2026-2030; and Cole et al. (1984) Mol. Cell Biol. 62: 109-120.)

Various methods such as Scatchard analysis in conjunction with radioimmunoassay techniques may be used to assess the affinity of antibodies for an antigen. Affinity is expressed as an association constant, $K_a$, which is defined as the molar concentration of antigen-antibody complex divided by the molar concentrations of free antigen and free antibody under equilibrium conditions. The $K_a$ determined for a preparation of polyclonal antibodies, which are heterogeneous in their affinities for multiple antigen epitopes, represents the average affinity, or avidity, of the antibodies for an antigen. The $K_a$ determined for a preparation of monoclonal antibodies, which are monospecific for a particular antigen epitope, represents a true measure of affinity. High-affinity antibody preparations with $K_a$ ranging from about $10^9$ to $10^{12}$ l/mole are preferred for use in immunoassays in which the antigen-antibody complex must withstand rigorous manipulations. Low-affinity antibody preparations with $K_a$ ranging from about $10^6$ to $10^7$ l/mole are preferred for use in immunopurification and similar procedures which ultimately require dissociation of antigen, preferably in active form, from the antibody. (See Catty (1988) Antibodies, Volume I: A Practical Approach, IRL Press, Washington, D.C.; and Liddell and Cryer (1991) A Practical Guide to Monoclonal Antibodies, John Wiley & Sons, New York, N.Y.)

Metal nanostructures are currently studied for a wide variety of biomedical applications including contrast imaging, ultrasonic imaging, thermal destruction of specific cancer cells, and laser tissue welding. All applications of this type rely on the optical and physical properties associated with metal nanoparticles, nominally of gold. Much of this work has focused on gold nanoshells due to their near IR optical absorption where tissue transmission is at its peak, making in-vivo applications feasible.

One of the most exciting of these applications is thermal destruction of cancer cells. The nanostructures are selectively attached to cancer cells in a tumor by a passive mechanism that has been termed an "enhanced permeability and retention effect". The tumor mass is then illuminated with near IR laser light which passes harmlessly through the tissue, but is absorbed strongly by the aggregates, causing them to heat drastically, killing only the cancerous cells. (See O'Neal et al., (2004) Cancer Lett. 209: 171-176, herein incorporated by reference in its entirety.) This technology has been utilized with gold-silica nanoshells further comprising "stealthing" polymers, such as poly(ethyleneglycol) and derives thereof, or liposomes; however this can be done better with HGNs of the present invention.

The nanostructures disclosed herein can be formed and shaped into a desired shape, such as a sphere, a cylinder, a rod, a rod, a cone, a pyramid, or other shape, not limited to regular shapes, and can be deposited upon a substrate at a desired density using means well known to those of skill in the art. (See, for example, Fan et al., (2005) J. Vac. Sci. Technol. 8: 947-953; Chaney et al., (2005) Appl. Phys. Lett. 87: pub. no. 031908.)

Nearly monodisperse HGNs of tunable interior and exterior diameter have been synthesized by sacrificial galvanic replacement of cobalt nanoparticles. We have been able to control the position of the surface plasmon band between 550 and 820 nm by carefully controlling particle size and wall thickness. Cobalt particle size, the sacrificial template that controls the resulting HGN size, is tunable by simultaneously changing the concentration of sodium borohydride and sodium citrate, the reductant and capping agent respectively. This varies from all previously reported aqueous syntheses of cobalt particles. We also show that by controlling the addition of gold carefully the thickness of the gold shell can be varied. These HGNs have been further demonstrated to be excellent SERS substrates in terms of spectral consistency. They are promising for chemical and biological sensing applications, particularly those requiring near IR absorption.

Effects of Oxygen on HGN Formation.

Figure 19:
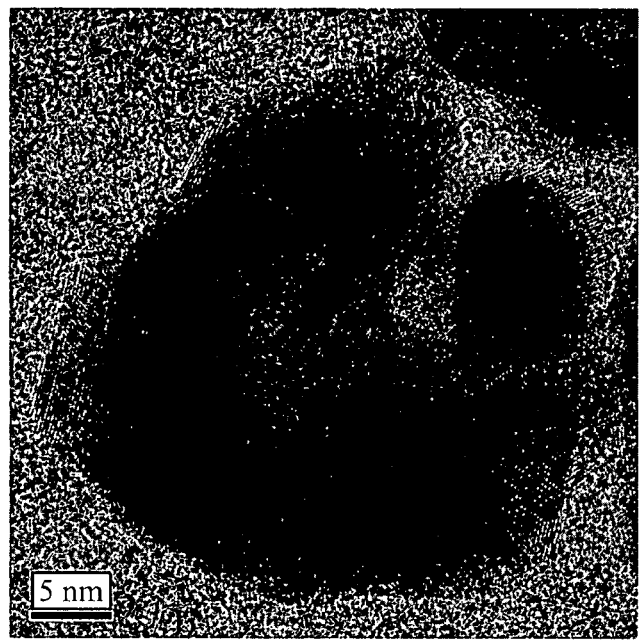
FIG. 19 is a high resolution TEM of an HGN formed from a slightly oxidized cobalt particle.

Cobalt is extremely sensitive to oxygen, especially in aqueous solution. If the solution is not properly de-oxygenated, or if air is allowed to enter the reaction vessel the results can be disastrous. While it is still possible to perform the reduction of gold salt on partially oxidized cobalt particles, it produces very poor results. The physical result of this is shown in FIG. 19. While the oxidized cobalt will dissolve in the solution, it does not oxidize homogeneously which results in malformed HGNs. Optically, this has extremely deleterious results greatly broadening the absorption band due to the random nature of the oxidation. When solutions are badly oxidized, the percentage of these types of particles tends to increase.

EXAMPLES

The invention will be more readily understood by reference to the following examples, which are included merely for purposes of illustration of certain aspects and embodiments of the present invention and not as limitations.

Example I

Synthesis of Hollow Gold Nanospheres

HGNs were synthesized by first producing cobalt nanoparticles as templates. 100 ml of 18 MΩ water, 500 µl of 0.1 M aqueous sodium citrate (Aldrich), and 100 μl of 0.4 M aqueous $CoCl_2$ (Aldrich) was degasses with nitrogen for 1 hour in a well sealed three neck flask. To this, 300 μl of a freshly prepared 1 M aqueous sodium borohydride (Aldrich) solution was added quickly. Hydrogen gas begins to form immediately and the solution turns from colourless to brown. The solution is allowed to stir under nitrogen for an additional 45 minutes to allow the sodium borohydride to completely react. While maintaining nitrogen flow, a 0.1 M aqueous chloroauric acid (Sigma-Aldrich, St. Louis, Mo.) solution is added in 50 μl aliquots to a final volume of 500 μl. The solution changes from brown, to red-purple, and is finally a deep blue color. Silver particles were synthesized by the method of Lee and Meisel (Lee, P. C.; Meisel, D., J. Phys. Chem. 1982, 86, 3391-3395).

Example II

Synthesis of Cobalt Nanoparticles

Cobalt nanoparticles were synthesized with the utmost attention paid to cleanliness and exclusion of air. All glassware was cleaned with alconox glassware detergent, then aquaregia to ensure the removal of all adsorbates, and then washed repeatedly with ultra-pure water. To ensure completely air free solutions, all solutions were vacuumed on a Schlink line until gas evolution ceased, then bubbled with ultra-pure argon for ten minutes. This process was repeated twice to remove as much oxygen as possible from the reaction vessel.

Fast Addition of Cobalt Chloride.

100 ml of water was placed into a three neck flask with 100-800 μl of a 0.1 M solution of sodium citrate or citric acid and deairated. To this, 100-800 μl of a freshly made 1M sodium borohydride solution was added. With rapid magnetic stirring, 100 μl of a 0.4 M-0.6 M cobalt chloride solution was added. Hydrogen immediately evolves and the solution changes from pale pink to brown/gray indicating the reduction of Co (II) into cobalt nanoparticles. This solution was allowed to react for between 15 and 60 minutes (under constant argon flow) depending on sodium borohydride concentration until hydrogen stopped evolving, indicating complete hydrolysis of the reductant. The addition of sodium borohydride and cobalt chloride was also performed in reverse order.

Slow Addition of Cobalt Chloride.

75 ml of water was placed in a 500 ml three neck flask with 400 μl of a 0.1 M solution of sodium citrate. 25 ml of water with 100 μl of 0.4 M cobalt chloride was placed in a 250 ml three neck flask. These two solutions were deairated. To the 500 ml three neck flask, 300 μl-400 μl of a freshly prepared 1M sodium borohydride solution was added. Using a cannula and argon gas to pressurize the 250 ml flask, the cobalt chloride solution was added dropwise at approximately 10 ml/minute. During this addition, the solution slowly changes from colorless to brown/gray signifying cobalt particle formation. This solution was allowed to react for 25 minutes to completely hydrolyze the sodium borohydride.

Example III

Gold Shell Growth

Due to the ease with which sodium borohydride is able to reduce the gold salt it is imperative that it be completely hydrolyzed before introducing gold. The presence of sodium borohydride is monitored by halting stirring and inspecting the solution for bubbles indicating the continuing hydrolysis of the reductant. It is only when bubbling has ceased completely that gold may be added.

High Concentration Addition.

Upon insuring complete hydrolysis of the sodium borohydride the flow of argon is increased and a 0.1 M solution of chloroauric acid is added at 50 μl/addition to a total volume between 150 μl and 450 μl. Between each addition 30 to 60 seconds are allowed to pass to ensure complete mixing. Upon completion of gold addition, the argon flow is stopped and the vessel is opened to ambient conditions under rapid stirring to oxidize any remaining cobalt metal left in solution.

Low Concentration Addition (Retaining Co at Core).

Using a cannula, 30 ml of the sodium borohydride free cobalt nanoparticle solution is transferred to an argon-purged graduated cylinder. This is then rapidly added to a vortexing 10 ml solution of chloroauric acid. The gold solution contains between 20-60 μl of cloroauric acid diluted to 10 ml. To retain the cobalt core this solution may be kept under argon flow, however, by exposing the solution to air the cobalt is completely oxidized leaving only water and dissolved salts at the core of the HGN. Samples with remaining cobalt cores retain a brown color, while oxidized samples change to between purple and green colored depending on amount of gold added and size of the particle.

Example IV

Single Particle SERS/Luminescence and Bulk SERS

Single particle SERS and Rayleigh scattering were performed on a home built confocal microscope system described previously (Schwartzberg, A. M., Grant, C. D., Wolcott, A., Talley, C. E., Huser, T. R., Bogomolni, R., and Zhang, J. Z., J. Phys. Chem. B 2004, 108, 19191-19197.) with the addition of transmitted light dark field illumination (NA 1 to 1.4). For SERS experiments and imaging, a Zeiss Apochromat 100×, 1.4 NA oil emersion objective was used. Typically the sample was integrated for 30 seconds with a total power of 100 mW from a helium-neon laser (632.8 nm, Melles Griot). Rayleigh scattering experiments were performed with a Zeiss Apochromat 100×, 0.7 NA oil emersion objective.

Samples for SERS and Rayleigh scattering were prepared by immobilizing the particles on glass coverslips with tri-methoxy-[3-(methylamino)propyl]silane (APS) (Aldrich). Coverslips were cleaned prior to the silanization step by sonication in a 2% solution of Hellmanex, followed by 18 MΩ water. They were then submerged in 5 mM aqueous solution of APS to deposit the tethering molecules. After one to two minutes, the coverslips were rinsed with water, dried under nitrogen, and 40 μl of the as prepared particle solution was placed on one surface. After several seconds exposed to the solution, it was rinsed with water then blown dry with nitrogen. For samples prepared for SERS studies, the HGNs coated surface was then treated with MBA by applying 40 μl of a 1 mM ethanoic solution for 60 seconds. The sample was then rinsed with ethanol and dried under nitrogen.

Figure 8:
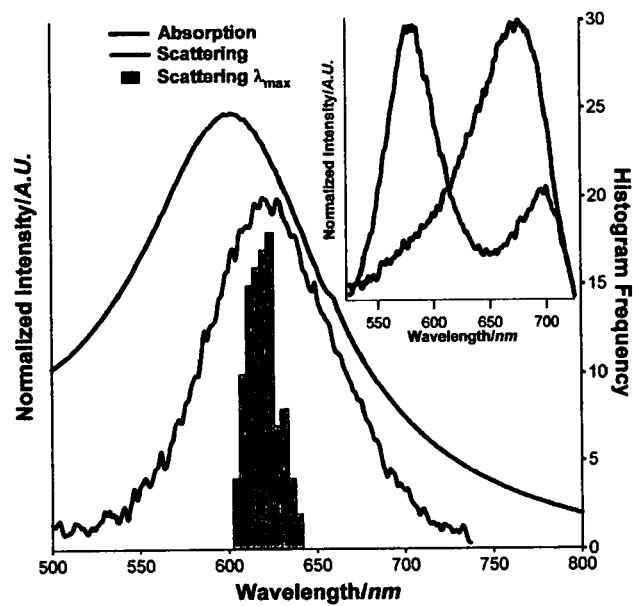
FIG. 8 illustrates the ensemble average solution absorption spectrum of an as prepared solution (black trace, top), and the Rayleigh scattering spectrum of a single HGNs (red trace, middle) immobilized on a glass coverslip in air. Plotted against the right axis is a histogram of the peak wavelength in the scattering spectra ($l_{max}$) of 100 particles (average 621±10.6 nm) (blue bars, bottom). The absorption spectrum is shifted in intensity for clarity. Inset: Rayleigh scattering spectra of two silver aggregates.

While questions remain about the nature of the enhancement at the HGNs surface, it is the consistency of their optical response that ultimately determines their reproducibility in sensor applications. To characterize the optical response, we began by examining the Rayleigh scattering spectra of many individual HGNs (FIG. 8, red trace, middle) and the ensemble average solution absorption (FIG. 8, black trace, top), both are indicative of plasmon resonance position and structure. Similar to other shell structures, a single peak is observed, nominally indicating non-aggregated HGNs (Nehl, C. L., Grady, N. K., Goodrich, G. P., Tam, F.; Halas, N. J., and Hafner, J. H., Nano Lett. 2004, 4, 2355-2359). The spectral width of the individual particle is not significantly different from that of the ensemble averaged solution, which is a result of the sample consistency. The shift of the peak position in the scattering spectrum as compared to that of the ensemble average solution absorption spectrum is due to a change in refractive index of the HGNs surrounding from air to water. This is known to affect the plasmon resonance of particles of this type. (See Nehl, C. L. et al., (2004) supra; Grady, N. K., Goodrich, G. P., Tam, F., Halas, N. J., and Hafner, J. H. Nano Lett., 2004, 4, 2355-2359. Sun, Y. G. and Xia, Y. N., Anal. Chem. 2002, 74, 5297-5305.)

The Rayleigh scattering spectra of 100 HGNs were taken and compiled (FIG. 8, bottom) into a histogram showing an average maximum scattering intensity ($\lambda_{max}$) of 621±10.6 nm. While there is some particle-to-particle variation it should not have an overly strong effect on the SERS response of the particles as the shift is less than 10% of the homogeneous line width. Any shift should have a minimal effect on the absorption cross-section at the excitation or Raman scattering wavelengths. This is clearly not the case with silver aggregates such as those shown in the inset of FIG. 8. The scattering of individual silver aggregates shifts drastically, by hundreds of nanometers, and many show multiple peaks.

Figure 4:
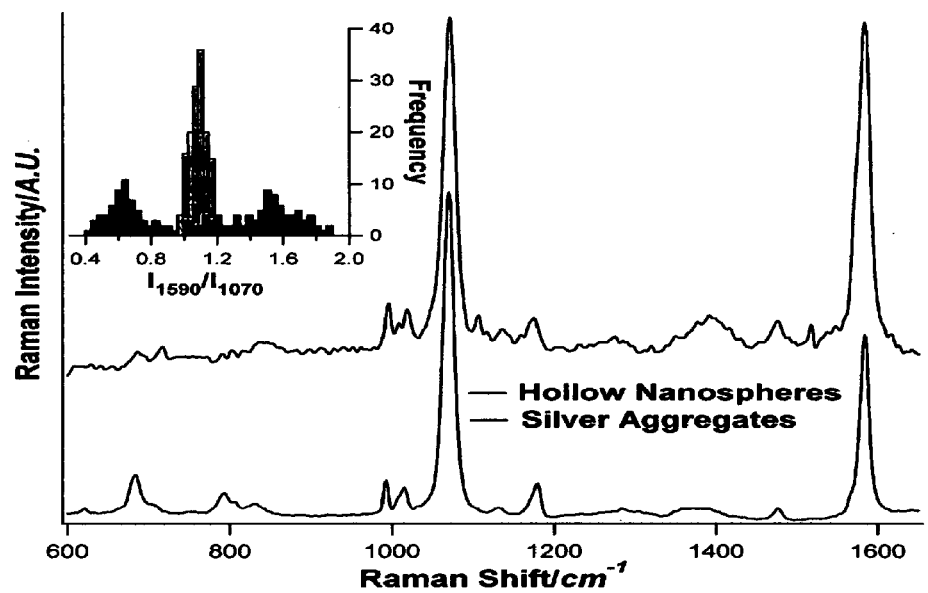
FIG. 4 shows a comparison of SERS spectrum consistency between HGNs and silver nanoparticles/aggregates. Shown are the single particle SERS spectrum of MBA on HGNs (red trace, top) and silver aggregates (blue trace, bottom). The inset is a histogram of the relative intensity of the two most intense peaks of MBA at 1070 $cm^{-1}$ and 1590 $cm^{-1}$ of 150 HGNs (red bars) and 150 silver aggregates (blue bars).

The homogeneous scattering properties of the HGNs suggest a consistent SERS response. To assess this, we compared the spectra of 150 HGNs and 150 standard silver particles coated with the same model analyte, 4-mercaptobenzoic acid (MBA). Representative SERS spectra of MBA bound to HGNs (red trace, top) and solid silver particles (blue trace, bottom) are shown in FIG. 4. The histograms in the inset show the statistical representation of the signal homogeneity of the silver (blue) and HGNs samples (red). To compare the two samples without the influence of absolute intensity fluctuations, two peaks were chosen to normalize the results. Peaks at 1070 cm$^{-1}$ and 1590 cm$^{-1}$, both ring breathing modes, were chosen because these are the most intense peaks. Also, they are spaced 500 cm$^{-1}$ apart where any variation due to plasmon shift should become readily apparent. From the histograms in the inset of FIG. 4, it is clear that the HGNs (red) have a significantly narrower distribution than the silver nanoparticles (blue). All peak ratios of the 150 HGNs fall within 0.9 and 1.1, representing statistical distribution of 5% by standard deviation, while the ratios for silver particles range from 0.5 to 1.7, or 45%. This is nearly a tenfold increase in consistency, demonstrating that these HGNs are a clear and significant improvement over the silver nanoparticle aggregates previously reported.

Figure 9:
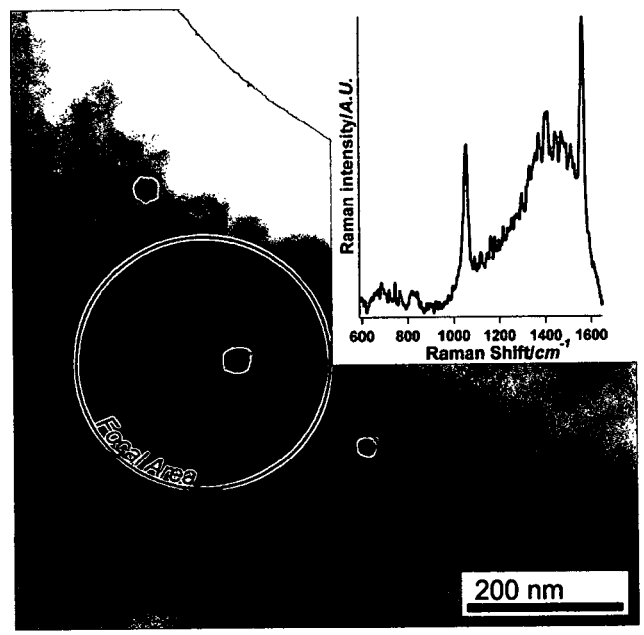
FIG. 9 is a TEM image of individual HGNs on a holey carbon TEM grid of which, the SERS spectrum has been measured (inset). TEM image was overlapped with confocal Raman images to co-locate the SERS active particles shown. Light region of the image is a hole in the film. Red circle marked "Focal Area" represents the approximate diameter of the laser focal area used to measure the SERS response of the sample.

Considering the importance of probe size, especially for intracellular sensing, it is imperative to confirm that single HGNs are sufficient to generate the observed SERS spectra, and not merely HGNs aggregates. All single particle experiments were performed with this in mind. By immobilizing particles to the surface of glass coverslips while taking steps to avoid aggregation we hope to minimize signal due to aggregated HGNs. To prove that enhancement can originate from individual HGNs, however, a more detailed and involved study was required. Single particles treated with the sample analyte MBA on indexed TEM grids were co-located by TEM and confocal Raman imaging. An area was located in which SERS was observed, while no aggregates were present within several hundred microns (FIG. 9). The diffraction limited focal area of the laser is indicated by the red circle, approximately 350 nm. The strong background of this spectrum is due to fluorescence of the holy carbon film on the TEM grid. While this fluorescence affects the appearance of the overall spectrum, it has little effect on the SERS spectrum of MBA that contains characteristic peaks, e.g. at 1070 cm$^{-1}$ and 1590 cm$^{-1}$. This is experiment clearly demonstrates that SERS can and does originate from individual hollow nanostructures.

Figure 10:
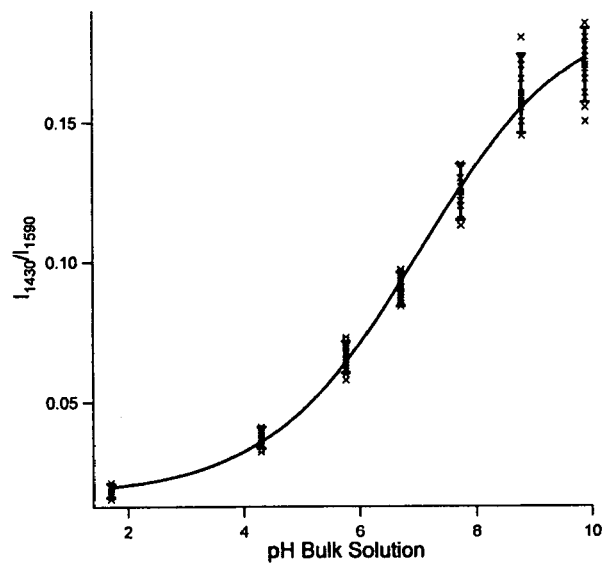
FIG. 10 represents each black point as the intensity of the pH sensitive 1430 $cm^{-1}$ peak of 20-30 particles at different pH normalized to the pH insensitive 1590 $cm^{-1}$ peak, while the red crosses are the individual data points. Error bars represent standard deviation of the measurements. The fit line is a guide to the eye.

The probe molecule used, MBA, was chosen for its utility as a model system in SERS pH sensing. SERS has the potential to become a valuable alternative approach to intracellular sensing compared to fluorescent dyes, because of its high sensitivity and molecular specificity. Even with resonant probe molecules, SERS provides robust signals that are not prone to rapid photodecomposition. In the following, we demonstrate that isolated functional gold nanostructures provide a highly consistent and reproducible SERS response for pH detection with a direct comparison to the aggregated silver colloids presented in earlier work (Talley, C. E., Jusinski, L., Hollars, C. W., Lane, S. M., and Huser, T., Anal. Chem. 2004, 76, 7064-7068). The response of MBA coated HGNs was taken at 7 different pH points with 20-30 particles sampled individually for each data point. The results are shown in FIG. 10 and represent a pH calibration curve. In FIG. 10, the SERS intensity ratio between the 1430 cm$^{-1}$ peak, due to COO$^-$ stretching mode and most sensitive to pH changes, and the 1590 cm$^{-1}$ ring breathing mode, which is insensitive to pH, is graphed as a function of different bulk pH. Error bars in the intensity ratio correspond to the standard deviation of each measurement and increase with signal intensity, as error is a function of enhancement variability and will linearly increase as the measured signal becomes larger. The percentage error is relatively constant through the entire pH range at an average of 9.1±2.4%. In a direct comparison to previous work, however, it is clear that for pH sensing applications, the HGNs are a significantly more precise probe than aggregated silver nanoparticles which have an average error of 104.5±71.6% (Talley, C. E. et al., (2004) supra); Jusinski, L., Hollars, C. W., Lane, S. M., and Huser, T., Anal. Chem. 2004, 76, 7064-7068). Again, this is a ten-fold improvement over the solid silver particle system.

The most important feature to note in FIG. 10 is the narrow distribution of relative intensities represented by the error bars at each measured pH value. The pH resolution is dependent on signal homogeneity of the probe. With nanoparticle aggregates, resolution was limited to about 1 pH unit due to the large variability resulting from the aggregated structures. With increased homogeneity of the HGNs, however, the resolution is now increased to 0.5 pH units or less, effectively doubling the sensitivity of the probe undoubtedly due to sample homogeneity and the ability to attain SERS from individual particles. In addition to this improvement in pH resolution, the HGNs are sensitive to a much broader pH range. While silver substrates yield a sensing region from ~pH 6.5-pH 8, these HGNs are responsive from ~pH 3.5-pH 9. The reason for this wider pH sensitivity is not immediately apparent, however, it is important to recognize that with increasing particle homogeneity, the packing of the MBA molecules at the particle surface will become more uniform. This will result in stronger molecule-molecule interactions that may have the effect of partially shielding some of the MBA from the bulk solution. This can shift the kinetics of the protonation or deprotonation process of the acid group, effectively expanding the window of sensitivity. By increasing the active range, this HGN-based probe is sensitive at most biologically relevant pH ranges.

Example V

Transmission Electron Microscopy (TEM)

Low resolution TEM measurements were performed on a JEOL model JEM-1200EX microscope and High resolution TEM was performed on a Philips CM300-FEG at the National Center for Electron Microscopy at Lawrence Berkeley National Laboratory.

Absorption measurements were taken on a HP 89532A spectrometer. All spectra were fit with Igor Pro 5.0 using a lorentzian function with chi square values less than 0.1. Particles were sized with imageJ image processing software (Abramoff, M. D., Magelhaes, P. J., and Ram, S. J., Biophotonics Internat. 2004, 11, 36).

Figure 6:
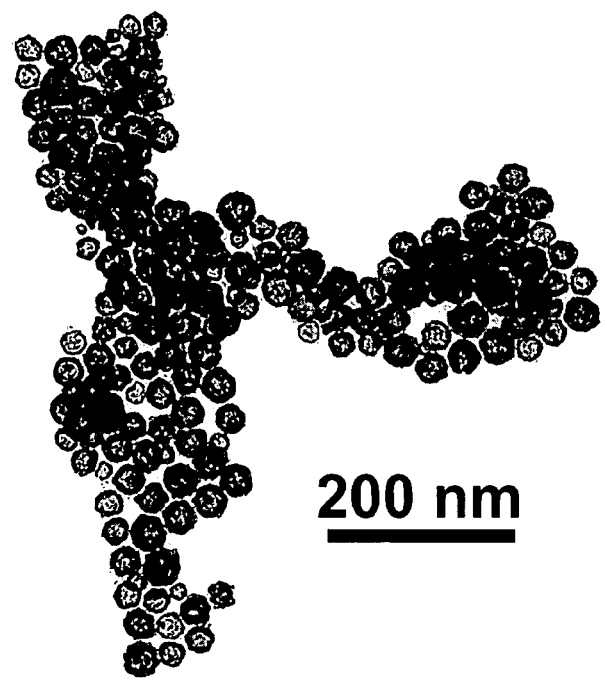
FIG. 6 is a representative low resolution TEM of HGNs. Examining 150 particles from such images, the mean size is found to be 30±4.5 nm.
Figure 7:
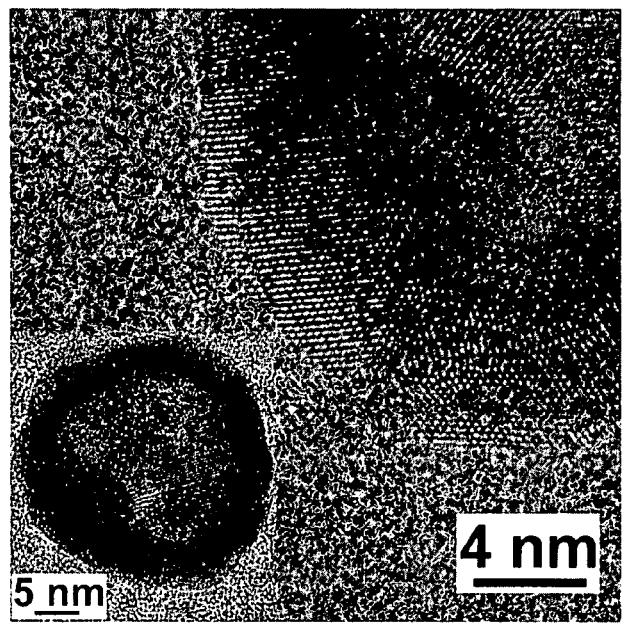
FIG. 7 is a high resolution TEM of an individual HGN of diameter 29.1 nm with approximately 5 nm wall thickness. Twinning in the HGN wall demonstrates its polycrystalline nature. A TEM of the whole HGNs is inset.

The homogeneity of the HGN samples is demonstrated in FIG. 6, which shows a representative low resolution transmission electron micrograph (TEM) of HGNs. The HGNs have an average diameter of 30 nm with a coefficient of variation of 14%. The relatively narrow size distribution is a reflection of the cobalt seed particles from which the HGNs were grown. The high resolution TEM of an individual HGN, shown in FIG. 7 illustrates the polycrystalline, and uniform nature of the HGNs. Twinning of the lattice planes confirms that the shell is comprised of nanocrystals that have been fused together upon growth. Due to the nature of wall growth, from the outside in, and the flow of oxidized cobalt out of, and gold ions into the HGNs, it is likely that pinholes in the wall will remain. Computationally, it has been shown that pinholes in hollow particle structures concentrate the evanescent field that results from the excitation of surface plasmons (Hao, E., Li, S. Y., Bailey, R. C., Zou, S. L., Schatz, G. C., and Hupp, J. T., J. Phys. Chem. B 2004, 108, 1224-1229). They are, however, difficult to detect by TEM measurement. This may be a factor important to SERS enhancement and will be explored in depth in future works.

Example VI

Effect of Cobalt Chloride, Sodium Borohydride and Sodium Citrate Concentration on Particle Size The goal of this study was to gain control of the cobalt particle size by aqueous solution chemical methods. Previous work on this system by Liang et al. focused more on the thickness of the shell to control its optical properties (Liang, H. P., Wan, L. J., Bai, C. L., and Jiang, L. J., Phys. Chem. B 2005, 109, 7795). While their work produced excellent results, further tunability is necessary to make the system as useful as possible. Initial attempts to reproduce the work of Liang et al. did not yield satisfactory results. The particles obtained were inhomogeneous and significantly smaller than the 60 nm reported. In fact, using as close to precisely the same synthesis as possible, ~25 nm cobalt particles were obtained, however, with their method of gold addition only inhomogeneous, gray solutions were observed. Upon determining an improved method of gold addition, this yielded excellent results for single particle SERS probes. However, there are many applications that may benefit from larger particle size and further red-shifted absorption, including SERS.

The other guiding hand in this work was provided by Kobayashi et al., who first reported this cobalt particle synthesis, but proceeded to cap the particles with silica shells to protect them from oxygen (Kobayashi, Y., Horie, M., Konno, M., Rodriguez-Gonzalez, B., and Liz-Marzan, L. M., J. Phys. Chem. B 2003, 107, 7420). Kobayashi et al. found that as citrate concentration was reduced, particle size increased. This is consistent with colloidal gold and silver syntheses and is not an unreasonable claim. For this application however, their trend did not hold true. A significant difference between this work and that of Kobayashi et al. is the time at which the reaction could be halted. In their work, for large cobalt particles, they were forced to add the silica growth reagents almost immediately upon reduction of the cobalt salt. Any delay at low citrate concentration and the solutions would become unstable and flocculate. In this work however, if the gold solution is added too quickly, it is immediately reduced by the remaining sodium borohydride instead of the cobalt particles. This leads to an unfortunate mess of nanoparticles. To achieve optimal particle growth a significant amount of time must pass in order to allow the sodium borohydride to completely hydrolyze before the gold can be added.

This being said, it is also important to note that even at relatively high concentrations of citrate where the particles are still stable after some time, there is little change in particle size by merely altering the citrate concentration. There may be a relatively simple explanation for this observation. Because the particle stability is directly related to the concentration of citrate there may have been an aggregation affect responsible for the size increase observed previously. As citrate concentration is reduced, we have observed that the rate of aggregation increased. Therefore, when capping the particles immediately after reduction, they are likely halting the aggregation at different stages depending on citrate concentration. When concentration is low, a larger aggregate will be formed before the silica can stabilize it, at high concentration a smaller aggregate will be present. This may be responsible for the lack of crystalline structure in the as synthesized particles. By sintering them at high temperature, they are likely fused into one crystalline particle.

Why then, does citrate not affect particle size as strongly as previously thought? In the case of colloidal gold, the reduction is done by the relatively weak reductant, citrate. This reaction is slow which allows for thermodynamic processes to control the formation of clusters. Only as many seed particles will be formed in the reaction as can be stabilized by the cappant/reductant. This means that the capping agent concentration will have a strong affect on the number of seed particles and hence, particle size. In the formation of cobalt particles however, a much stronger reducing agent is required. As sodium borohydride is a significantly stronger reductant than is technically required to reduce the cobalt salt to cobalt metal, the reduction is extremely fast, taking place in less than one minute as opposed to five to ten minutes for the reduction of gold salt by citrate. Because of this, kinetic processes dominate the formation of seed particles. The number of seeds, and therefore the size of the resulting particle, will be more dependent on the rate of the reduction.

The rate of reduction can be controlled in several ways. Temperature plays a strong role in the rate of reaction, however, little change in particle size was observed between particles synthesized at 0° C. and room temperature. A second way to alter rate is by changing the solution pH. The reductive potential of sodium borohydride is pH dependent. It is important to note at this point that contrary to previous reports of this synthesis, we use sodium citrate instead of citric acid. This is because the reaction was found to be slower at the higher pH, and particle homogeneity was superior in the neutral solution. Higher and lower pH was also attempted by adjusting with HCl and NaOH. These solutions, however, were unstable and immediately crashed out. This is most likely due to the presence of excess ions, especially $Cl^-$ which has a strong disrupting effect on aqueous colloidal capping. Finally, altering the concentration of reductant was used to change reaction rate. This was found to be the best method of controlling particle size without drastically decreasing particle homogeneity.

By decreasing the amount of sodium borohydride present, the reaction time is increased substantially. This produces larger particles that remain stable in solution. Table 1 shows the result of varying sodium borohydride concentration by one quarter. The particle size is increased by approximately 40%, however, this is the practical limit of size tunability by this method. Lower concentrations produce incredibly inhomogeneous results that are often unstable. In order to form larger particles we must also alter the sodium citrate concentration.

TABLE 1

Particle size is dependent upon sodium borohydride concentration

| Volume 0.4M $CoCl_2$ (μl) | Volume 0.1M Citrate (μl) | Volume 1M $NaBH_4$ (μl) | Particle Size (nm) |
|---|---|---|---|
| 100 | 400 | 400 | 31 ± 2 |
| 100 | 400 | 100 | 44 ± 5 |

All reactions were performed in 100 ml water. All particle sizes are determined by examining the resulting gold particles. Reported sizes are in diameter.

Figure 11:
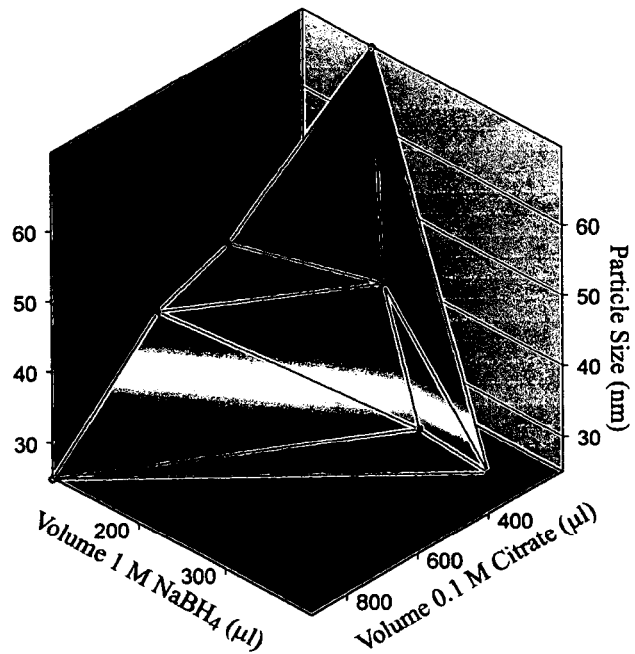
FIG. 11 illustrates particle size as a function of citrate and sodium borohydride concentration. All particle sizes are determined by examining TEM images of the resulting gold structures and represent the measurement of at least 200 particles. Reported sizes are the particle diameter.

While the sodium borohydride reduction of metal salts is largely kinetics driven, there are still some thermodynamic-type processes controlling particle size. This is especially true as the concentration of reductant is decreased and the reaction is slowed. The reaction is now substantially more thermodynamically controlled, making the variation in capping agent concentration more effective in controlling particle size. By decreasing both $NaBH_4$ and citrate concentration we observed a drastic increase in particle size, this is shown in the 3D plot in FIG. 11. The trend appears to be linear, at least within the concentrations shown here. At lower concentrations the particle sizes could be substantially larger, however, because they crash out of solution almost immediately this is not something we could test. We present this as a general method of tuning the size of cobalt nanoparticles. Using this plot, it is possible to predict roughly what the final particle size will be at a given sodium borohydride and sodium citrate concentration.

Example VII

The Influence of the Rate of Addition and Concentration of $CoCl_2$ on Particle Homogeneity To increase particle homogeneity and size, a slow addition of low concentration cobalt salt was attempted. It was thought that this would artificially slow the rate of reaction. This, however, was not the case, as is shown in Table 2.

TABLE 2

Rate of addition and concentration of cobalt salt influences particle size.

| Rate of $CoCl_2$ Addition | $CoCl_2$ Concentration (M) | Volume 0.1M Citrate (μl) | Volume 1M $NaBH_4$ (μl) | Particle Size (nm) |
|---|---|---|---|---|
| Fast | 0.4 | 400 | 400 | 28 ± 2 |
| Slow | 0.4 (diluted) | 400 | 400 | 31 ± 6 |
| Fast | 0.5 | 400 | 400 | 50 ± 5 |

All particle sizes are in diameters. The cobalt chloride solution used for the slow addition is diluted to 25 ml with water.

Figure 12:
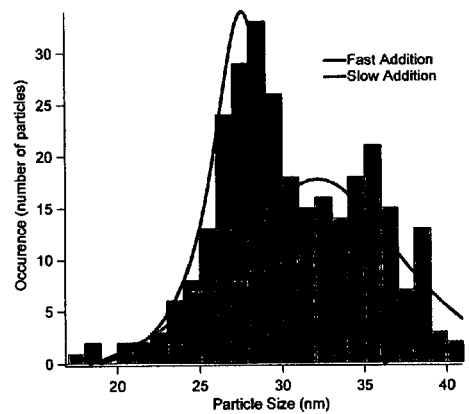
FIG. 12 illustrates histograms showing the size dispersion of cobalt nanoparticles produced by slow and fast addition of cobalt chloride. Solid lines are best fits demonstrating particle dispersion. Particles sizes determined by measuring low resolution TEM images.

While slightly larger particles were achieved, the coefficient of variation increases from 7% to 18%. This is clearly not an advantageous method of controlling particle size. The reason for this great increase in variation is due to the continual formation of seed particles as the cobalt is added. When examining the particles it is obvious that some seeds are formed initially and result in very large particles, while others are formed throughout the addition and lead to small particles. This is clear in FIG. 12 that shows histograms of particle size from slow and fast addition of cobalt. Not only does this exemplify the inhomogeneity of the slow addition sample, it also shows the asymmetric formation of particles. While the fast addition yields a nice, even sample, the slow addition yields a curve broadened and asymmetrically shifted by the presence of large particles formed early in the cobalt addition. This is clearly not the way to increase particle size. By increasing the concentration of cobalt while maintaining volume, however, we have found that particle size changes drastically without excessively broadening particle distribution, this is also shown in Table 2. While higher concentrations of cobalt seem to induce flocculation, it may be possible to better control this with careful changes in citrate concentration.

Example VIII

Formation of Gold Shells

Figure 13:
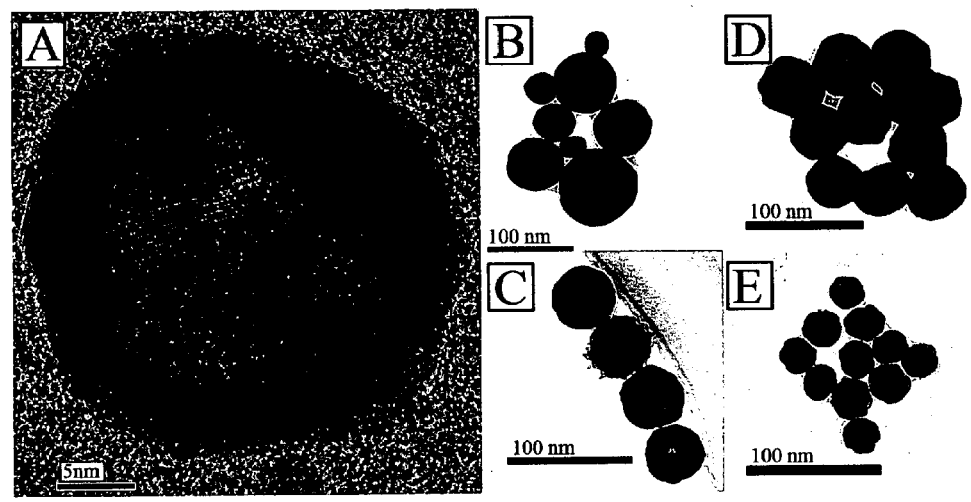
FIG. 13 show transmission electron micrographs of the HGNs.
Figure 14:
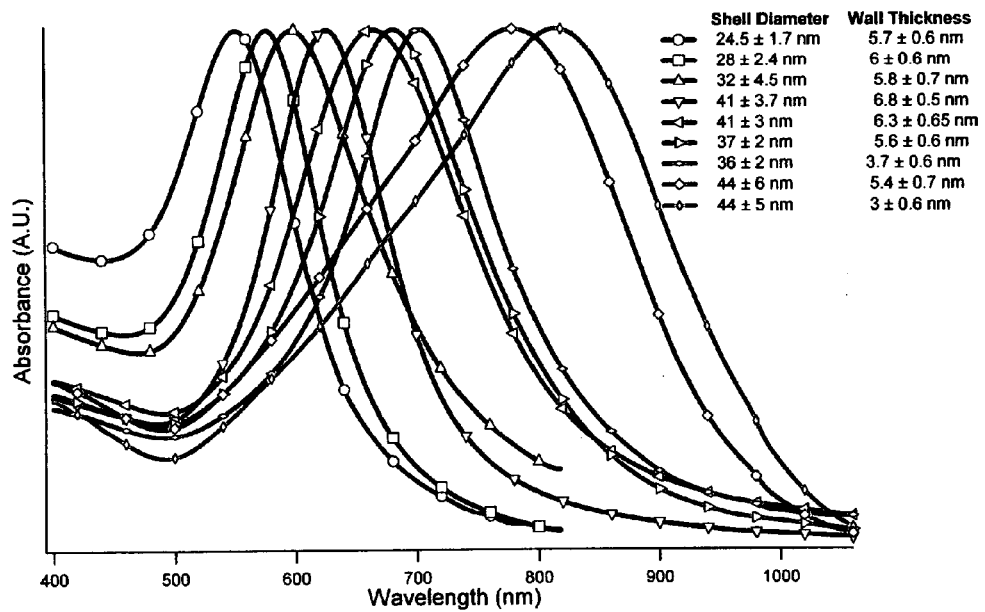
FIG. 14 illustrates the UV-visible absorption spectra of nine HGN samples with varying shell diameters and wall thicknesses.
Figure 15:
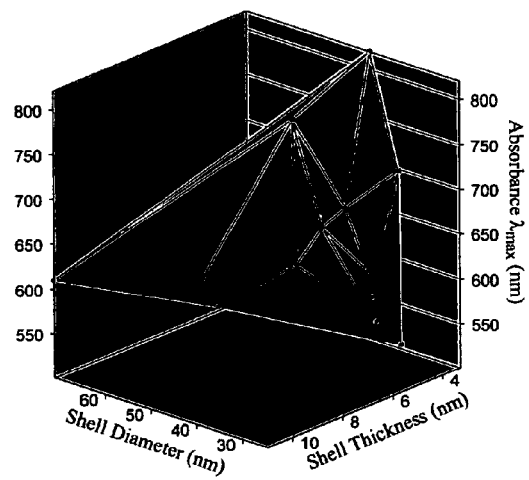
FIG. 15 shows plasmon absorbance maximum wavelength ($\lambda_{max}$) as a function of shell thickness and shell diameter. Each point represents an individual set of experiments and represents the average measured lengths.
Figure 16:
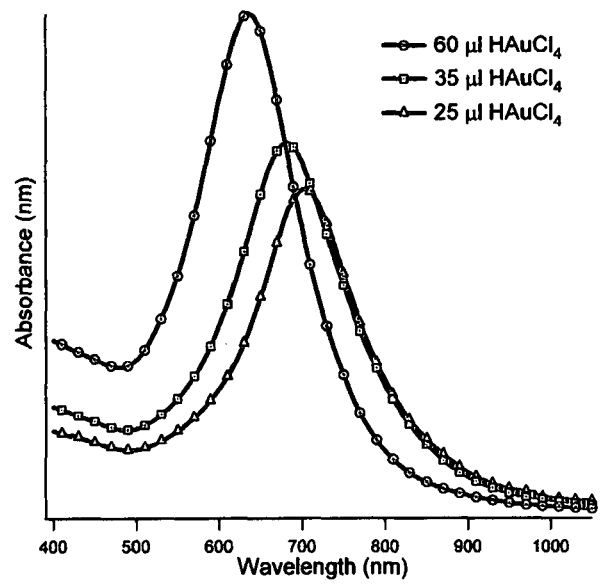
FIG. 16 illustrates spectral dependence on volume of added gold salt. Gold solutions were diluted to 10 ml with water before 30 ml of a cobalt solution made by the fast cobalt addition method with 100 μl sodium borohydride and 600 μl of citric acid. Average particle size is 35±2 nm.

Along with the tunability of cobalt particle sizes we have been able to produce a wide variety of sizes of the HGNs as shown in FIG. 13. These are representative TEM images of the HGNs at different sizes. FIG. 13A is a high resolution TEM of a 30 nm particle, the lattice fringes of gold are clearly defined and show that these particles are poly-crystalline with large single crystalline areas. FIGS. 13B-F show the tunability of the samples, from 70 nm to 28 nm. The largest particle sample in FIG. 13B clearly demonstrates the inhomogeneity that seems to be inherent at larger sizes.

Forming the gold shell seems to be an extremely simple matter at first glance, however, under closer inspection it becomes clear that there are many parameters that must be carefully controlled in order to form high quality samples. As mentioned above, attempting to recreate the previous works did not result in good samples. Another method was needed to make homogeneous samples of high optical and structural quality like those shown in FIG. 13.

High Concentration Gold Addition.

The general consensus on homogeneous nanoparticle formation is that a low concentration of reagents yields the best results. It is important to remember, however, that in the addition of gold here, we are not forming a normal colloidal nanoparticle system. All that determines particle size and shape is the sacrificial template. For this reason the high concentration addition of gold should not necessarily produce poor results. After many attempts, it was found that by adding high concentration (0.1 M) gold salt in small volumes yielded excellent results. Adding the gold all at once gave poor results, as did adding the solution dropwise. By using approximately 50 μl per addition over five to eight additions, spectrally narrow, highly concentrated samples were achieved.

The explanation for this is a fairly simple one: it is a matter of mixing. The reaction of gold salt with the cobalt particle is very fast, happening almost instantaneously upon the addition of the gold. There is also a secondary shell mediated growth that takes place on a slightly longer time scale, where free citrate in solution will reduce excess gold salt onto the formed shells. This can result in significantly thicker shells when too much gold is added. When a small amount of gold is introduced to the stirred solution, all particles at the site of the addition will immediately be oxidized completely in the presence of such high concentration gold. If there is excess gold at this site, it will diffuse through the solution being reduced onto the cobalt particles until there is no more gold. If the volume of gold solution is too low, i.e. dropwise, the immediate impact will be relatively small but due to the small size of the droplet it will dilute quickly. As the gold dilutes into the water, less and less will be reduced onto the cobalt, resulting in a gradient of shell thicknesses. Thickest at the site of addition and thinner shells moving away from the concentration center. This leads to an incongruous sample in which some shells are badly under-formed and some are over-grown by seed mediated growth. An excellent example of this overgrowth is in FIG. 13C. The second particle from the top has some slight over-growth that looks like small particle stuck to the surface. When the concentration is excessive this becomes a much more pronounced feature of the particle.

At the other end of the addition rate scale is the all-at-once addition of the gold. This suffers similar problems to the drop-wise addition, however, there is significantly more overgrowth, and less under-formed particles. We were able to overcome this problem by using a middle of the road approach. By using 50 µl per addition the resulting particles were uniform and we did not observe excessive over-growth. The choice of this volume was not obvious and was only discovered by experimental trials. This method does, however, have one major flaw. Because such high concentrations are used, we were not able to readily control the shell thicknesses. In theory, if the gold is added correctly, the shell thickness should be a function of the amount of gold added. This was achieved by using relatively large volumes of low concentration gold.

Low Concentration Gold Addition.

It was determined early on in this study that using low concentrations of gold would not produce satisfactory results; however, this assessment was not entirely correct. Several factors are required for the low concentration addition of gold to work properly. The first is that the solution should be mixed very well, as quickly as possible. If the cobalt is added to the gold solution too slowly, most of the gold will be utilized by a small number of particles, which will lead to poor sample homogeneity. Second, the volume of the gold salt to which the cobalt is added must be large enough that mixing can happen very quickly. With low volumes of gold at higher concentrations there is still a pronounced mixing problem, leading to poor samples. This is the problem we observed in reproducing the work of Liang et al. (Liang et al. (2005) supra). While the larger volumes of gold produced reasonable results, using 5 ml or 8 ml of gold salt gave widely varying results and consistency was a major issue. Because mixing is the biggest issue in producing consistent results, it was hypothesized that by holding the volumes of gold and cobalt solutions constant, a more consistent result could be obtained.

By diluting varying volumes of gold salt to 10 ml with water and adding the cobalt as quickly as possible under rapid stirring we were able to produce homogeneous HGN with tunable wall thicknesses, similar to the work of Liang et al. (Liang et al. (2005) supra). Shell thickness varies linearly with gold concentration, indicating that homogeneous mixing is taking place, as shown in Table 3. These are representative values from a single sample and are consistent with all other data.

TABLE 3

Wall thickness as a function of the volume of gold salt added

| Volume of 0.1M HAuCL$_4$ Dilluted to 10 ml (µl) | Volume 0.1M CoCl$_2$ (µl) | Volume 0.1M Citrate (µl) | Volume 1M NaBH$_4$ (µl) | Particle Size (nm) | Wall Thickness |
|---|---|---|---|---|---|
| 25 | 100 | 600 | 100 | 40 ± 6 | 6.2 ± 0.6 |
| 35 | 100 | 600 | 100 | 40 ± 6 | 6.9 ± 0.8 |
| 60 | 100 | 600 | 100 | 40 ± 6 | 8 ± 0.7 |

Example IX

Effect of Particle Size and Wall Thickness on Optical Properties

One of the major intents of all this size tuning is the control of the optical properties of the HGN. We have found that by varying wall thickness and particle size it is possible to tune the plasmon absorption across much of the visible spectrum as in FIG. 4. These spectra are representative of many experiments and show the full range of tunability of this system. While the full width half max (FWHM) of the spectra remains relatively unchanged from 500 to 750 nm at between 50 and 100 nm, the last two spectra are fairly broadened to over 200 nm. This is likely due to the formation of gold shells and rings. These are shells that have not completely formed and are likely red shifted in absorption from the complete shells. The weak shoulder at 700 nm may be due to the presence of complete shells, while the peak is due to the rings. At this time, however, it is not possible to determine the exact affect of the presence of the rings.

By increasing particle size at a constant wall thickness the absorption band will red-shift as the plasmon oscillation decreases in energy. On the other hand, increasing wall thickness at constant particle size will blue shift the absorption band. The band shifts to higher energy because as the inner diameter of the HGN decreases, it takes on more solid particle like properties. As solid gold particles at these sizes have plasmon bands at approximately 520 nm, the absorption will always shift in this direction as wall thickness increases. This is predicted in the work of Hao et al. and is shown experimentally here in FIG. 4 (Hao, E., Li, S. Y., Bailey, R. C., Zou, S. L., Schatz, G. C., and Hupp, J. T., J. Phys. Chem. B 2004, 108, 1224). This 3D plot shows the effect of particle size and wall thickness on plasmon absorption. Representing thirteen independent experiments, the trend is clearly shown here. Because the work of Hao et al. is for particle of different sizes than those made here, we are not able to directly correlate their results to our data. However, we are currently working on similar calculations that should determine if these results match well to the theory.

Because wall thickness plays such an important role in the position of the plasmon absorption, it is important to understand how this corresponds to the amount of gold added to the solution. FIG. 5 shows the non-normalized absorption spectra of three samples made from a single batch of 35 nm cobalt nanoparticles. The highest concentration sample, at 60 µl of 0.1 M gold salt added absorbs most strongly at 638 nm, is the most blue shifted of the three as would be expected and has a wall thickness of 7±0.8 nm. The lower concentration samples at 35 ml and 25 ml are red shifted to 685 nm (wall thickness 5.6±0.6 nm) and 702 nm (wall thickness 3.7±0.6 nm) respectively. Interestingly, as the band shifts the FWHM changes only slightly from 80 nm for the 60 µl sample, to 91 nm for the 35 µl sample to 82 nm for the 25 µl sample. This is not the trend one might expect given the propensity of solid gold nanoparticles to broaden significantly in spectrum with increasing size. This broadening is due to the introduction of new multi-pole modes which are non-radiative and broader in energy than the normal dipole plasmon mode (Payne, E. K., Shuford, K. L., Park, S., Schatz, G. C., and Mirkin, C. A., J. Phys. Chem. B 2006, 110, 2150; Millstone, J. E., Park, S., Shuford, K. L., Qin, L. D., Schatz, G. C., and Mirkin, C. A., J. Am. Chem. Soc. 2005, 127, 5312). In fact, upon close examination of FIG. 13 it is clear that with the exception of the last two spectra, the FWHM changes little regardless of particle size or shell thickness. The explanation for this is tied to the electron mean free path in gold. Because the wall thickness is much less than this length, (~50 nm) longer axes will dominate the plasmon oscillations and the multi-pole modes which require large particles will be minimized. Interestingly, this also explains why only one absorption band is observed for this system, while nanorods, which also have multiple axes of oscillation, will show two.

It may be noted that as the concentration of gold added decreases, there is a decrease in optical density as well. This is not a matter of particle concentration, since 10 ml of gold is added to each sample, and the total number of HGNs is fixed to the number of cobalt particles present in the original solution. This is a function of absorption cross section of the HGNs due to the different thicknesses of gold. As the wall grows thicker it will have a larger absorption cross section.

Example X

Homogeneous Line Width and Inhomogeneous Broadening

Figure 17:
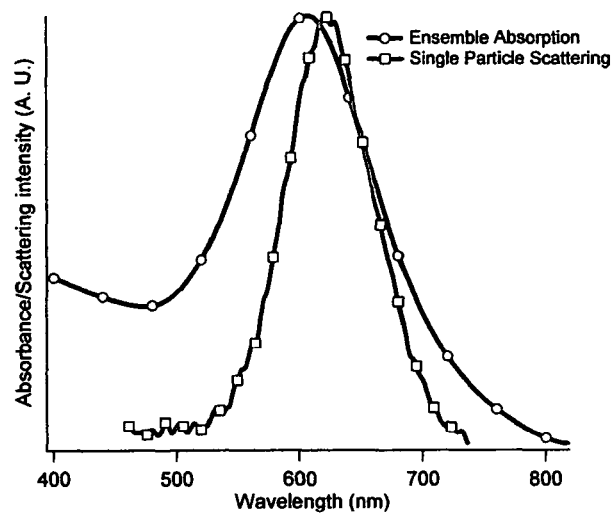
FIG. 17 illustrates a comparison of ensemble averaged absorption and single particle Rayleigh scattering of 30±2.6 nm HGNs.

To determine if, and to what extent the absorption spectrum is broadened by inhomogeneity in the sample, we examined the Rayleigh scattering spectra of the HGNs. While the FWHM of the ensemble averaged solution of 30±2.6 nm particles is 75 nm, the single particle FWHM is 47 nm as shown in FIG. 17. This is a broadening of 27 nm that shows that the samples are slightly inhomogeneously broadened. This is to be expected to some point, but is impressively small considering how sensitive these structures are to variance in wall thickness and local environment (Nehl, C. L., Grady, N. K., Goodrich, G. P., Tam, F., Halas, N. J., and Hafner, J. H., Nano Lett. 2004, 4, 2355; Sun, Y. G. and Xia, Y. N., Anal. Chem. 2002, 74, 5297). The sensitivity to local environment is clear upon examination of the spectral shift between the ensemble averaged and scattering spectra. This is a shift of 14 nm and is consistent with all particles examined. The scattering spectra were taken from particles immobilized on glass substrates in air while the ensemble-averaged spectra were taken in aqueous solution. The refractive index of the imbedding medium decreases from 1.33 to 1 in going from water to air in these two scenarios. This substantially changes the optical properties of the HGNs. A decrease in refractive index has been shown to correspond to a red shift, and explains our observations here.

Example XI

Surface Enhanced Raman Scattering

Figure 18:
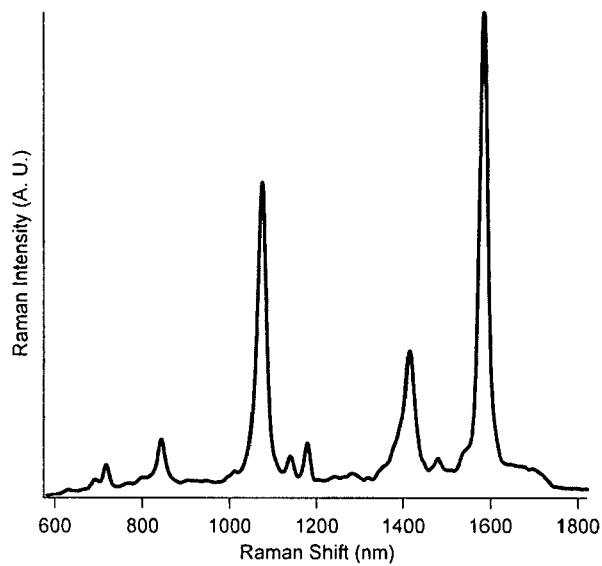
FIG. 18 illustrates the ensemble averaged surface enhanced Raman scattering spectrum of mercaptobenzoic acid on the HGNs.

SERS experiments were performed on solutions of as prepared HGNs with mercaptobenzoic acid (MBA) added to a final concentration of 1 mM. At this concentration there was no spectral shift observed which would indicate aggregation, therefore we can nominally say that the resulting spectra are from non-aggregated or at least minimally aggregated. This was confirmed in our previous work on SERS of single HGNs that showed that enhancement is observable from non-aggregated HGNs (Schwartzberg, A. M., Olsen, T. Y., Huser, T. R., Zhang, J. Z., and Talley, C. E., Anal. Chem. 2006, 78, 4732-4736). Here we show the ensemble averaged SERS spectrum of MBA in FIG. 18. In terms of enhancement, when compared in the SERS intensity to aggregated Lee and Meisel silver particles, the standard high enhancement SERS substrate, we achieve about 10% of the signal. This is an excellent result for nominally non-aggregated particles and significantly better than many current single particle systems.

Example XII

Synthesis of Metal Nanotube

Hollow gold nanotubes were synthesized by an electroless deposition on semi-ordered, aggregated cobalt nanoparticles. The formation of cobalt nanoparticles and the electroless deposition of gold has been reported previously, however, in order to form nanotubes, reaction conditions are altered slightly. (See Schwartzberg, A. M., Olson, T. Y., Talley, C. E. and Zhang, J. Z., J. Phys. Chem. B 110, 19935-19944 (2006); Liang, H. P., Wan, L. J., Bai, C. L. and Jiang, L., J. Phys. Chem. B 109, 7795-7800 (2005).)

Briefly, 100 ml of 18 MΩ purified water with 100 µl of a 0.5 M $CoCl_2$ aqueous solution and 600 µl of a 0.1 M aqueous sodium citrate solution was degassed in a round bottom three neck flask under vacuum and purged with nitrogen three times to ensure an oxygen free environment. To this, 100 µl of a 1 M aqueous $NaBH_4$ solution was added under vigorous magnetic stirring. Hydrogen evolution was immediate and subsequently the solution changed in color from light pink to light brown/gray. This cobalt nanoparticle solution was allowed to stir under nitrogen for 35-40 minutes until hydrogen evolution ceased to insure that all sodium borohydride was reacted. To form the gold nanotubes, 30 ml of the stock cobalt nanoparticle solution was added to 10 ml of rapidly mixing water with 25 µl of 1 mM $HAuCl_4$ solution. This same procedure was also followed in the absence of magnetic stirring to determine the effect of the magnetic field on the nanotube formation. In this case manual swirling of the reaction vessel was used.

Low resolution TEM measurements were performed on a JEOL model JEM-1200EX microscope and High resolution TEM was performed on a Philips CM300-FEG at the national center for electron microscopy at Lawrence Berkeley National Laboratory.

Example XIII

Detection of Ab-GNP Binding Interaction Using a Secondary Ab

The effect of binding an antigen to its antibody is observed by taking the Raman spectrum of the antibody before and after exposure to the antigen through the use of SERS. To study the applicability of this method, a primary antibody (SC2020, Santa Cruz Biotechnology Santa Cruz Calif.) and a secondary antibody (SC1616, Santa Cruz Biotechnology Santa Cruz Calif.) were used. SC2020 was obtained at a concentration of 400 µg/ml and diluted by a factor of two with 20 mM HEPES buffer (pH 7.4). This solution was mixed equal volume with a GNP solution that was also diluted by a factor of two with 20 mM HEPES buffer. After twenty minutes of interaction, a SERS spectrum was obtained. An equal amount of SC1616 was added to the system and the SERS spectrum was obtained again. The binding of the secondary antibody (SC1616) to the primary antibody (SC2020) caused the SERS intensity of the secondary antibody to increase by 20-50%. This method provides an indirect means of detecting antigens in a system.

Example XIV

Detection of Tumour-Antigens in Bodily Fluids

A murine monoclonal antibody raised against the CA125 ovarian cancer marker (OC125; Bast et al., (1981) J. Clin. Invest. 68: 1331-1337; Cat. No. AB19551, AbCam Ltd., Cambridge, UK) is incubated at a final concentration of 100 µg/ml in HEPES buffer (pH 7.4) with GNA as prepared above at a final concentration of 1 mg/ml for twenty minutes at ambient temperature. The mixture is then washed four times with excess sample buffer, then stored at 4° C. until use. A fraction is subjected to SERS to obtain baseline values.

Fluid samples from individuals with diagnosed ovarian cancer are incubated with SQD in the presence of a conjugating agent and linker molecule for 20 minutes at ambient temperature. The mixture is washed four times and resuspended in HEPES buffer (pH 7.4) to produce SQD-Ag conjugate. A fraction is subjected to SQD luminescence to obtain baseline values.

The SQD-Ag conjugate is added to OC125-GNA mixture in HEPES incubation medium (pH 7.4) at ambient temperature for 8 hours. Control samples are from individuals without diagnosed disease or disorders. The samples are then washed four times with incubation medium, resuspended in sample buffer, and then divided into two fractions. One fraction is subjected to SQD luminescence. The other fraction is subjected to SERS. Baseline values obtained earlier are then compared with the values obtained under experimental conditions.

Example XV

Production of Antigen Specific Antibodies

Antigen substantially purified using polyacrylamide gel electrophoresis (PAGE; see, for example, Harrington (1990) Methods Enzymol. 182: 488-495) or other purification techniques is used to immunize rabbits and to produce antibodies using standard protocols. The antigen amino acid sequence is analyzed using DNASTAR software (DNASTAR Inc., Madison Wis.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, for example, Ausubel et al. supra, chapter 11.)

Typically, the oligopeptides are 15 residues in length, and are synthesized using an Applied Biosystems Peptide Synthesizer Model 431A using Fmoc-chemistry and coupled to KLH (Sigma-Aldrich, St. Louis, Mo.) by reaction with N-maleimidobenzoyl-N-hydroxysuccinimide ester to increase immunogenicity. (See, for example, Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG. In the alternative, a non-peptide antigen is used and is conjugated to KLH.

Example XVI

Purification of Naturally Occurring Antigen Using Specific Antibodies

Naturally occurring or recombinant antigen is substantially purified by immunoaffinity chromatography using antibodies specific for the antigen. An immunoaffinity column is constructed by covalently coupling anti-antigen antibody to an activated chromatographic resin, such as CNBr-activated Sepharose (Pharmacia & Upjohn, Kalamazoo Mich.). After the coupling, the resin is blocked and washed according to the manufacturer's instructions.

Media containing antigen are passed over the immunoaffinity column, and the column is washed under conditions that allow the preferential absorbance of antigen (for example, high ionic strength buffers in the presence of detergent). The column is eluted under conditions that disrupt antibody/antigen binding (for example, a buffer of pH 2 to pH 3, or a high concentration of a chaotrope, such as urea or thiocyanate ion), and antigen is collected.

Example XVII

Identification of Molecules that Interact with Antigen

Antigen, or biologically active fragments thereof, are labeled with [$^{125}$I] Bolton-Hunter reagent. (See, for example, Bolton and Hunter (1973) Biochem. J. 133: 529-539.) Candidate molecules previously arrayed in the wells of a multi-well plate are incubated with the labeled antigen, washed, and any wells with labeled antigen complex are assayed. Data obtained using different concentrations of antigen are used to calculate values for the number, affinity, and association of antigen with the candidate molecules.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A synthetic nanotube, the synthetic nanotube comprising a substantially homogenous polycrystalline uniform symmetrical metal nanostructure, the synthetic nanotube being substantially hollow and having dimensions of between about 20 nm and 100 nm in diameter and at least between about 0.1 µm and 4 µm in length, the synthetic nanotube further comprising a surface and at least one detecting molecule, and wherein the detecting molecule is bound to the surface.

2. The synthetic nanotube of claim 1 wherein the synthetic nanotube comprises a metal selected from the group consisting of gold, silver, platinum, copper, aluminum, palladium, cadmium, iridium, and rhodium.

3. A conduit for conducting fluids, the conduit comprising the synthetic nanotube of claim 1.

4. An electronic conductor, the electronic conductor comprising the synthetic nanotube of claim 1.

5. A method for detecting an analyte in a sample using a chemical sensor comprising the synthetic nanotube of claim 1, the method comprising the steps of: i) providing a sample; ii) providing a semiconductor quantum dot comprising a linker molecule (LM-SQD); iii) conjugating the analyte in the sample with the LM-SQD thereby producing an analyte-LM-SQD conjugate; iv) providing a chemical sensor comprising the synthetic nanotube, the synthetic nanotube having at least one surface and wherein the shell comprises a gold molecular species, the shell surface further comprising a detecting molecule; v) incubating the analyte-LM-SQD conjugate with the chemical sensor for a predetermined time period; and vi) measuring the extent of binding between the analyte-LM-SQD conjugate and the chemical sensor; thereby detecting the analyte in the sample.

6. The method of claim 5, wherein the sample is selected from the group consisting of mammalian cells, vertebrate cells, invertebrate cells, plant cells, fungal cells, mold cells, archaeal cells, bacterial cells, viruses, and bacteriophages.

7. The method of claim 5, wherein the sample is selected from the group consisting of blood fluids, lymph fluids, hemolymph fluids, pulmonary surfactant fluids, peritoneal fluids, gastric fluids, xylem fluids, and phloem fluids.

8. The method of claim 5, wherein the sample is selected from the group consisting of fluvial fluids, marine fluids, atmospheric precipitate fluids, waste-water fluids, agricultural run-off fluids, fluids comprising hydrocarbons, fluids contaminated by hydrocarbons, aerosol fluids, aqueous fluids, and non-aqueous fluids.

* * * * *